(12) United States Patent
Deigin et al.

(10) Patent No.: US 9,718,869 B2
(45) Date of Patent: Aug. 1, 2017

(54) PEPTIDE-BASED COMPOUNDS AND USES THEREOF TO TREAT BETA-AMYLOID ACCUMULATION

(71) Applicant: MANUS PHARMACEUTICALS (CANADA) LTD., Toronto (CA)

(72) Inventors: Vladislav Deigin, Toronto (CA); Olga Volpina, Moscow (RU); Natalia Bobkova, Moscow (RU)

(73) Assignee: MANUS PHARMACEUTICALS (CANADA) LTD., Toronto, ON (CA)

( * ) Notice: Subject to any disclaimer, the term of this patent is extended or adjusted under 35 U.S.C. 154(b) by 0 days.

(21) Appl. No.: 14/416,956

(22) PCT Filed: Jul. 24, 2013

(86) PCT No.: PCT/IB2013/056082
§ 371 (c)(1),
(2) Date: Jan. 23, 2015

(87) PCT Pub. No.: WO2014/016787
PCT Pub. Date: Jan. 30, 2014

(65) Prior Publication Data
US 2015/0337026 A1 Nov. 26, 2015

Related U.S. Application Data

(60) Provisional application No. 61/675,205, filed on Jul. 24, 2012.

(51) Int. Cl.
*A61K 38/00* (2006.01)
*C07K 14/705* (2006.01)
*A61K 47/48* (2006.01)
*A61K 39/00* (2006.01)

(52) U.S. Cl.
CPC .... *C07K 14/70571* (2013.01); *A61K 39/0007* (2013.01); *A61K 47/48246* (2013.01); *A61K 47/48284* (2013.01); *A61K 38/00* (2013.01)

(58) Field of Classification Search
None
See application file for complete search history.

(56) References Cited

FOREIGN PATENT DOCUMENTS

| RU | 2372355 C1 | 11/2009 |
|----|------------|---------|
| WO | 0214351 A2 | 2/2002 |
| WO | WO 02/14351 * | 2/2002 |
| WO | WO 2008/014613 | 2/2008 |

OTHER PUBLICATIONS

Peng et al (Mol Pharmacol. Mar. 1994;45(3):546-54).*
International Search Report and Written Opinion dated Nov. 11, 2013 for corresponding PCT Patent Application No. PCT/IB2013/056082.
Volpina O.M., et al., "Production of antibodies to the alpha7-subunit of human acetylcholine receptor with the use of immunoactive synthetic peptides", Bioorganicheskaya Khimiya, 32, 2006, 169-175. (English summary of Russian text).
Giunta, Brian, et al., "Antiretroviral Medications Disrupt Microglial Phagocytosis of β-amyloid and Increase its Production by Neurons: Implications for HIV-associated Neurocognitive Disorders", Molecular Brain, 4, 2011, 1-6.
Loane, David J., et al., "Modulation of ABCA1 by an LXR Agonist Reduces Beta-Amyloid Levels and Improves Outcome after Traumatic Brain Injury", J. Neurotraum., 28, 2011, 225-236.
McKee, Ann C., et al., "Chronic Traumatic Encephalopathy in Athletes: Progressive Tauopathy Following Repetitive Head Injury", J. Neuropathol Exp Neurol., 68, 2009, 709-735.
Netzer, William J., et al., "Lowering β-Amyloid Levels Rescues Learning and Memory in a Down Syndrome Mouse Model", PLoS ONE, 5, 2010, 1-5.
Zhang, Yong, et al., "Mutant Ubiquitin-Mediated β-secretase Stability via Activation of Caspase-3 is Related to β-amyloid Accumulation in Ischemic Striatum in Rats", J. Cerebr. Blood. F. Met., 30, 2010, 566-575.
Zhang, Yusheng, et al., "Reduction of β-amyloid Deposits by γ-secretase Inhibitor is Associated with the Attenuation of Secondary Damage in the Ipsilateral Thalamus and Sensory Functional Improvement after Focal Cortical Infarction in Hypertensive Rats", J. Cerebr. Blood. F. Met., 31, 2011, 572-579.
Achim, Cristian L. Achim, et al., "Increased Accumulation of Intraneuronal Amyloid β in HIV-Infected Patients", J. Neuroimmune Pharmacol, 2009, 4, pp. 190-199.
Behl, Mamta, et al. "Lead-Induced Accumulation of β-Amyloid in the Choroid Plexus: Role of Low Density Lipoprotein Receptor Protein-1 and Protein Kinase C", Neurotoxicology, 2010, September, 31(5), pp. 524-532.
Chen, Guiquan, et al., "Active β-Amyloid Immunication Restores Spatial Learning in PDAPP Mice Displaying Very Low Levels of β-Amyloid", The Journal of Neuroscience, Mar. 7, 2007, 27(10), pp. 2654-2662.
Xu, Jiqing, et al., "The comorbidity of HIV-associated neurocognitive disorders and Alzheimer's disease: a foreseeable medical challenge in post-HAART era", J. Neuroimmune Pharmacol., Jun. 2009, 4(2), pp. 200-212.
Extended European Search Report issued in European patent application No. 13823250.9, dated Jul. 26, 2016.
Kamynina et al., "Acetylcholine and antibodies against the acetylcholine receptor protect neurons and astrocytes against beta-amyloid toxicity," *International Journal of Biochemistry and Cell Biology*, 45(4):899-907, 2013.

(Continued)

*Primary Examiner* — James H Alstrum Acevedo
*Assistant Examiner* — Sergio Coffa
(74) *Attorney, Agent, or Firm* — Parker Highlander PLLC

(57) ABSTRACT

The present application relates to novel peptide-based compounds, optionally comprising an immunoactive built-in adjuvant, compositions comprising these compounds and their use, in particular for the treatment of diseases, disorders or conditions characterized by or associated with β-amyloid accumulation. In particular, the present application includes compounds of Formula I, and compositions and uses thereof: $[R^a\text{-NP}]_m\text{-L}_p$ (I).

20 Claims, 5 Drawing Sheets

(56) References Cited

OTHER PUBLICATIONS

Kamynina et al., "Vaccination with peptide 173-193 of acetylcholine receptor α7-subunit prevents memory loss in olfactory bulbectomized mice," *Journal of Alzheimer's Disease*, 21(1):249-261, 2010.

* cited by examiner

A.

B.

A.

B.

PEPTIDE-BASED COMPOUNDS AND USES THEREOF TO TREAT BETA-AMYLOID ACCUMULATION

The present application is a national phase application under 35 U.S.C. §371 of International Application No. PCT/IB2013/056082, filed Jul. 24, 2013, which claims the benefit of priority to U.S. Provisional Patent Application No. 61/675,205, filed Jul. 24, 2012.

The sequence listing that is contained in the file named "BEPAP0013US_ST25.txt", which is 7 KB (as measured in Microsoft Windows®) and was created on Jan. 28, 2015, is filed herewith by electronic submission and is incorporated by reference herein.

FIELD OF THE APPLICATION

The present application relates to novel peptide-based compounds, optionally comprising an immunoactive built-in adjuvant, compositions comprising these compounds and their use, in particular for the treatment of diseases, disorders or conditions characterized by or associated with β-amyloid accumulation.

BACKGROUND OF THE APPLICATION

Alzheimer's disease (AD) is a severe neurodegenerative disease that leads to memory loss, mental illness and inevitable death. One of the modern hypotheses suggests that amyloid β-peptides, in particular, βA-(1-42), by binding to α7-acetylcholine receptor (AChR), form clusters in the form of amyloid plaques and lead to the destruction of brain tissue.

Elevated β-amyloid levels have also been reported in Down syndrome (DS) patients throughout their life, and are believed to cause AD in adults with DS.[1] The results of a mouse study suggested intellectual disability in young DS patients might be treatable by Aβ-lowering drugs. 1 A transient cerebral ischemia can also significantly increase β-amyloid generation.[2]

Deposition of Aβ-plaques has been reported to be a common pathological feature of HIV infection.[3] It has been suggested that antiretroviral therapy (ART) may play a role in the elevated Aβ found in the brain of persons infected with HIV, and consequently these compounds may contribute to the cognitive decline observed in HIV associated neurocognitive disorders (HAND).[3]

Traumatic brain injury (TBI) has also been reported to increase brain β-amyloid in humans and animals.[4] Post-mortem studies of TBI victims have shown that approximately 30% have Aβ deposits.[5] Evidence suggests these deposits are formed rapidly after injury; within 24 h of the initial impact.[6]

Abnormal β-amyloid deposits in the thalamus have been reported after cerebral cortical infarction, and are suggested to be associated with secondary thalamic damage.[7]

Deposition of β-amyloid, most commonly as diffuse plaques has also been reported in cases of chronic traumatic encephalopathy (CTE) following repetitive head injury, but has only been reported to occur in fewer than half the cases studied.[8]

Today there exist several drugs that are used for the symptomatic treatment of AD. These drugs can, to some extent, delay the progression of the disease but not cure it. The most widely used class of drugs for the symptomatic treatment of AD therapy are compensatory cholinesterase inhibitors. However, the effectiveness of cholinesterase inhibitors is significantly reduced in the later stages of AD. Also, cholinesterase inhibitors are characterized by relatively high toxicity and a number of other side effects.[9] There are also other medications for the symptomatic treatment of AD.[10]

An important drawback of the compensatory therapy is that these drugs do not address the currently believed root cause of AD-β-amyloid accumulation. Therefore, intensive research is being conducted to find a way to address that root cause. It has been previously shown that an intermediate stage in the accumulation of βA in the cell is the formation of its complex with the type α7 AChRs.[11]

Russian Federation patent no. 2372355 of Jun. 27, 2008 describes the peptide (NP-1) of the sequence:

[SEQ ID NO: 1]
Glu-Trp-Asp-Leu-Val-Gly-Ile-Pro-Gly-Lys-Arg-Ser-
Glu-Arg-Phe-Tyr-Glu-Cys-Cys-Lys-Glu which is the 173-193 fragment of the α7-subunit of the human acetylcholine receptor (AChR). Immunization by the above synthetic peptide produced antibodies capable of binding to the type α7 AChRs thereby preventing the formation of the complex sβA and, consequently, the formation of amyloid plaques. In behavioural tests, immunization with NP-1 prevented deterioration of spatial memory in animals with experimentally induced AD and prevented an increase in brain levels of βA. Also, immunization with NP-1 did not lead to deterioration of spatial memory in healthy animals.

The drawback of NP-1 (synthetic peptide 173-193) was that it was only active when administered in conjunction with complete Freund's adjuvant (a substance that stimulates the creation of antipeptide antibodies by the host's immune system), whose application in medical practice is not allowed. Therefore, a desirable feature when creating a pharmaceutical preparation for the immunotherapy of diseases, disorders or conditions characterized by or associated with β-amyloid accumulation such as Alzheimer's disease, is the creation of peptide structures that are immunogenic and have protective activity without the use of complete Freund's adjuvant.

SUMMARY OF THE APPLICATION

In the present application, it has been demonstrated that a peptide fragment of NP-1 conjugated to keyhole limpet hemocyanin (KLH) is capable of preserving spatial memory in bulbectomized mice. Bulbectomization is a process that is known to initiate an Alzheimer's like neurodegenerative process thus providing an in vivo model for studying the effects of test compounds for treating this disease.

To develop peptide-based compounds such as NP-1 and peptide fragments of NP-1 possessing immunogenicity without conjugation to protein carriers such as KLH or bovine serum albumin (BSA), new peptide-based compounds comprising moieties responsible for stimulating immune response and antibody production have been developed and are reported herein. Compounds of the application have been shown to be capable of stimulating antibody formation and reducing levels of β-amyloid in the brain of bulbectomized mice as compared to control animals, without being administered in combination with complete Freund's adjuvant. Compounds of the application have also been shown to preserve spatial memory in bulbectomized mice.

Accordingly, the present application includes a compound of Formula I:

$$[R^a\text{-}NP]_m\text{-}L_p \qquad (I)$$

wherein

NP is a sequence comprising at least 9 contiguous amino acids of Glu-Trp-Asp-Leu-Val-Gly-Ile-Pro-Gly-Lys-Arg-Ser-Glu-Arg-Phe-Tyr-Glu-Cys-Cys-Lys-Glu [SEQ ID NO:1], optionally with conservative amino acid substitutions or amino acid analog substitutions thereof, or NP is a deletion or addition analog of [SEQ ID NO:1], optionally with conservative amino acid substitutions or amino acid analog substitutions thereof;

m is 1 or 2;
p is 0 when m is 1 and p is 1 when m is 2;
L is a linker group;
$R^a$ is H or a group of the formula:

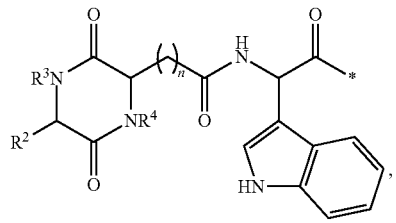

wherein
* represents the site of attachment to NP;
n is 1 or 2;
$R^2$ is $C_{1-6}$alkyl or $C_{1-3}$alkylenePh; and
$R^3$ and $R^4$ are independently selected from H and $C_{1-4}$alkyl, provided that when $R^a$ is H and m is 1, NP is not [SEQ ID NO:1], or pharmaceutically acceptable salts thereof.

The present application also includes a compound selected from:

```
WDLVGIPGKRSERFYECCKE;    [SEQ ID NO: 2]

DLVGIPGKRSERFYECCKE;     [SEQ ID NO: 3]

LVGIPGKRSERFYECCKE;      [SEQ ID NO: 4]

VGIPGKRSERFYECCKE;       [SEQ ID NO: 5]

GIPGKRSERFYECCKE;        [SEQ ID NO: 6]

IPGKRSERFYECCKE;         [SEQ ID NO: 7]

PGKRSERFYECCKE;          [SEQ ID NO: 8]

GKRSERFYECCKE;           [SEQ ID NO: 9]

KRSERFYECCKE;            [SEQ ID NO: 10]

RSERFYECCKE;             [SEQ ID NO: 11]

SERFYECCKE;              [SEQ ID NO: 12]

ERFYECCKE;               [SEQ ID NO: 13]

EWDLVGIPGKRSERFYECCK;    [SEQ ID NO: 14]

EWDLVGIPGKRSERFYECC;     [SEQ ID NO: 15]

EWDLVGIPGKRSERFYEC;      [SEQ ID NO: 16]

EWDLVGIPGKRSERFYE;       [SEQ ID NO: 17]

EWDLVGIPGKRSERFY;        [SEQ ID NO: 18]

EWDLVGIPGKRSERF;         [SEQ ID NO: 19]

EWDLVGIPGKRSER;          [SEQ ID NO: 20]

EWDLVGIPGKRSE;           [SEQ ID NO: 21]

EWDLVGIPGKRS;            [SEQ ID NO: 22]

EWDLVGIPGKR;             [SEQ ID NO: 23]

EWDLVGIPGK;              [SEQ ID NO: 24]

EWDLVGIPG;               [SEQ ID NO: 25]

WDLVGIPGK;               [SEQ ID NO: 26]

EWDLVGIPGKRSERFY;        [SEQ ID NO: 27]
and

IPGKRSERFY,              [SEQ ID NO: 28]
``` or any one [SEQ ID NO:2] to [SEQ ID NO: 28] in which one or more of the amino acids has been substituted with a conservative amino acid analog thereof, or pharmaceutically acceptable salts thereof.

The present application also includes a composition comprising one or more of the compounds of the application and a carrier. In an embodiment, the composition is a pharmaceutical composition comprising one or more compounds of the application and a pharmaceutically acceptable carrier. In another embodiment, the composition further comprises an adjuvant. It is an embodiment that the adjuvant is incomplete Freund's adjuvant.

The compounds of the application have been shown to be capable of stimulating antibody formation and reducing levels of β-amyloid in bulbectomized mice. Therefore the compounds of the application are useful for treating diseases, disorders or conditions characterized by or associated with β-amyloid accumulation. Accordingly, the present application also includes a method of treating diseases, disorders or conditions characterized by or associated with β-amyloid accumulation, comprising administering a therapeutically effective amount of one or more compounds of the application to a subject in need thereof.

In a further embodiment, the compounds of the present application are used as medicaments. Accordingly, the application also includes a compound of the application for use as a medicament.

The present application further includes a use of one or more compounds of the application for treating diseases, disorders or conditions characterized by or associated with β-amyloid accumulation as well as a use of one or more compounds of the application for the preparation of a medicament for treating diseases, disorders or conditions characterized by or associated with β-amyloid accumulation. Finally, the application also includes one or more compounds of the application for use in treating diseases, disorders or conditions characterized by or associated with β-amyloid accumulation.

In embodiments of the application, the diseases, disorders or conditions that are characterized by or associated with β-amyloid accumulation include Alzheimer's disease, Down syndrome, transient cerebral ischemia, HIV infection, traumatic brain injury, cerebral cortical infarction and chronic traumatic encephalopathy.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The present application will now be described in greater detail with reference to the drawings in which.

DETAILED DESCRIPTION OF THE APPLICATION

I. Definitions

Figure 1:
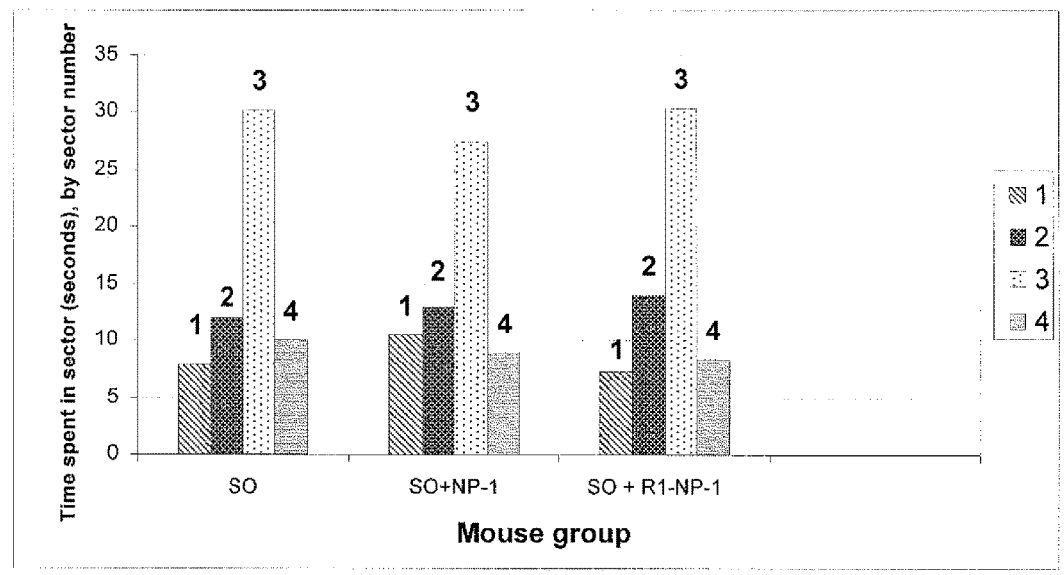
FIG. 1 shows the effect of immunization with NP-1 and R-1-NP-1 on the spatial memory of sham operated (SO) mice: (A) data by time spent in the sectors of the Morris water maze; (B) data by relative number of sector visits, expressed as a percentage relative to the total number of all sector visits (calculated individually for each animal then aggregated for the group). Sector 3 contained the rescue platform during training.
Figure 1:
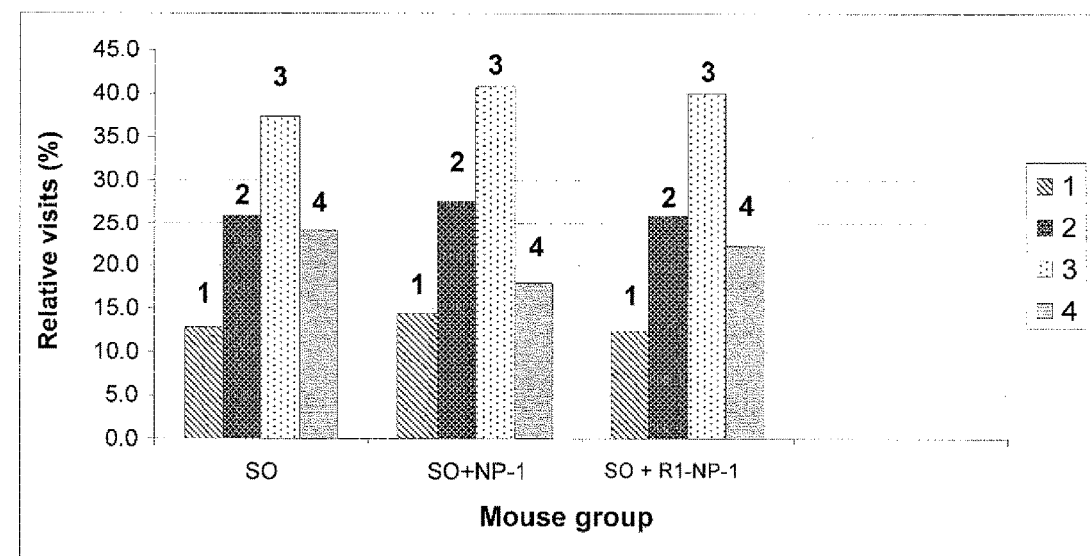

Unless otherwise indicated, the definitions and embodiments described in this and other sections are intended to be applicable to all embodiments and aspects of the application herein described for which they are suitable as would be understood by a person skilled in the art.

The term "alkyl" as used herein, whether it is used alone or as part of another group, means straight or branched chain, saturated alkyl groups. The term $C_{1-6}$alkyl means an alkyl group having 1, 2, 3, 4, 5 or 6 carbon atoms.

The term "alkylene" as used herein, whether alone or as part of another group, means an alkyl group that is bivalent; i.e. that is substituted on two ends with another group.

The term "linker" refers to a chemical grouping that connects other chemical groupings. Many chemical linking groups are known in the art. A linking group will generally have a functional group at opposing ends that allows it to react with the chemical groupings being linked. For example, when linking two amino acid groups together, a linking group will have, on opposing ends, functional groups that will form a covalent bond with an amino group or a carboxylic acid, or alternatively with a functional group in an amino acid side chain. Such functional groups include, for example, amines, carboxylic acids, thiols, acid chlorides, hydroxyls, and the like. In an embodiment, the linker group is an amino acid. In another embodiment, the linker group is a di-hydroxy or di-amino $C_{1-20}$alkylene.

As used in this application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "compound of the application" or "compound of the present application" and the like as used herein refers to a compound of Formula I, and pharmaceutically acceptable salts thereof, as well as a compound selected from [SEQ ID NO: 2] to [SEQ ID NO:28], conservative amino acid analogs thereof and pharmaceutically acceptable salts thereof.

The term "subject" as used herein includes all members of the animal kingdom including mammals, and suitably refers to humans.

The term "pharmaceutically acceptable" means compatible with the treatment of subjects, in particular humans.

The term "pharmaceutically acceptable salt" means an acid addition salt or a base addition salt which is suitable for, or compatible with, the treatment of subjects.

An acid addition salt suitable for, or compatible with, the treatment of subjects is any non-toxic organic or inorganic salt of any basic compound. Basic compounds that form an acid addition salt include, for example, compounds comprising an amine group. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid in a suitable solvent and the formed salt is isolated by filtration, extraction or any other suitable method.

In embodiments of the application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early Alzheimer's disease can be treated to prevent progression, or alternatively a subject in remission can be treated with a compound or composition described herein to prevent recurrence. Treatment methods comprise administering to a subject a therapeutically effective amount of one or more of the compounds of the application and optionally consists of a single administration, or alternatively comprises a series of administrations. For example, the compounds of the application are administered at least once a week. However, in another embodiment, the compounds are administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, the age of the patient, the concentration, the activity of the compounds of the application, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration is required. For example, the compounds are administered to the subject in an amount and for a duration sufficient to treat the patient.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition characterized by or associated with β-amyloid accumulation or manifesting a symptom associated with a disease, disorder or condition characterized by or associated with β-amyloid accumulation or a reduction in the risk or probability of β-amyloid accumulation.

As used herein, the term "effective amount" or "therapeutically effective amount" means an amount effective, at dosages and for periods of time necessary to achieve the desired result. For example in the context of treating a disease, disorder or condition characterized by or associated with β-amyloid accumulation, an effective amount is an amount that, for example, reduces β-amyloid accumulation compared to the β-amyloid accumulation without administration of the compound. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective dose of a compound or composition of the application to a cell either in cell culture or in a subject.

The term "amino acid" refers to naturally occurring and non-naturally occurring amino acids, as well as amino acid analogs and amino acid mimetics that possess similar structural, chemical and/or functional characteristics to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Reference to an amino acid includes, for example, naturally occurring proteogenic L-amino acids as well as D-amino acids. Standard single letter or three letter notations have been used as follows:

A—Ala—alanine
C—Cys—cysteine
D—Asp—aspartic acid
E—Glu—glutamic acid
F—Phe—phenylalanine
G—Gly—glycine
H—His—histidine
I—Ile—Isoleucine
K—Lys—lysine
L—Leu—leucine
M—Met—methionine
N—Asn—asparagine
O—Pyl—pyrrolysine
P—Pro—proline
Q—Gln—glutamine
R—Arg—arginine
S—Ser—serine
T—Thr—threonine
U—Sec—selenocysteine
V—Val—valine
W—Trp—tryptophan
Y—Tyr—tyrosine.

The expression "amino acid analogs" as used herein, including non-naturally occurring amino acids and modified naturally occurring amino acids, refers to compounds that have the same basic chemical structure as a naturally occurring amino acid, i.e., a carbon that is bound to a hydrogen, a carboxyl group, an amino group, and an R group, and includes, for example, homoserine, norleucine, methionine sulfoxide and methionine methyl sulfonium. Such analogs have modified R groups (such as, norleucine) or modified peptide backbones, but retain the same basic chemical structure as a naturally occurring amino acid. Amino acid analogs include chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid). The incorporation of amino acid analogs, such as non-natural amino acids, including synthetic non-native amino acids or substituted amino acids, may be advantageous in a number of different ways.

The terms "polypeptide," "peptide" and "protein" refer to a polymer or oligomer of amino acid residues. The terms apply to naturally occurring amino acid polymers as well as amino acid polymers in which one or more amino acid residues are a non-naturally encoded amino acid. As used herein, the terms encompass amino acid chains of any length, including full length proteins, wherein the amino acid residues are linked by covalent peptide bonds. The polypeptides, peptides and proteins are written using standard sequence notation, with the nitrogen terminus being on the left and the carboxy terminus on the right.

The term "conservative amino acid substitutions" refers to all substitutions wherein the substituted amino acid has similar structural, chemical and/or functional properties with the corresponding amino acid in the reference sequence. By way of example, conservative amino acid substitutions involve substitution of one aliphatic or hydrophobic amino acid, e.g., alanine, valine, leucine, isoleucine, methionine, phenylalanine, or tryptophan with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, and glycine, with another. Conservative substitution tables providing functionally similar amino acids are known to those of ordinary skill in the art.

The term "deletion analog" refers to an amino acid sequence that comprises one or more less amino acids than the reference amino acid sequence. In particular the deletion analog comprises 1, 2, 3, 4, 5, 6, 7, 8, 9, 10, 11 or 12 amino acids less than the reference amino acid sequence. In all cases, the deletion analog will retain at least a portion of the activity of the reference amino acid sequence therefore the deleted amino acids are those that do not affect the function of the reference amino acid sequence.

The term "addition analog" refers to an amino acid sequence that comprises one or more amino acids than the reference amino acid sequence. In particular the addition analog comprises 1, 2, 3, 4, 5, 6, 7, 8, 9 or 10 amino acids more than the reference amino acid sequence. In all cases, the addition analog will retain at least a portion of the activity of the reference amino acid sequence therefore the added amino acids are those that do not affect the function of the reference amino acid sequence.

The term "Freund's adjuvant" or "complete Freund's adjuvant" or CFA as used herein refers to a water-in-oil emulsion comprising non-metabolizable oils, for example paraffin oil and mannide monooleate and an inactivated *Mycobacterium* species, for example *M. tuberculosis*. The term "incomplete Freund's adjuvant" or IFA as used herein lacks the inactivated *Mycobacterium* species. Freund's adjuvant and IFA are commercially available, for example from Sigma-Aldrich Co.

Ph as used herein refers to the group phenyl.

The term "NP-1" as used herein refers to a peptide of the sequence:

[SEQ ID NO: 1]
Glu-Trp-Asp-Leu-Val-Gly-Ile-Pro-Gly-Lys-Arg-Ser-
Glu-Arg-Phe-Tyr-Glu-Cys-Cys-Lys-Glu.

The term "R-1-NP-1" as used herein refers to a compound of Formula I:

$$[R^a\text{-NP}]_m\text{-}L_p \qquad (I),$$

wherein m is 1, p is 0, NP is NP-1, and $R^a$ is a group of the formula:

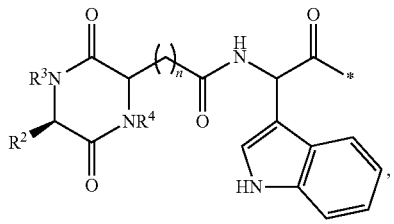

wherein * represents the site of attachment to NP, n is 2, $R^2$ is $CH_3$, and $R^3$ and $R^4$ are both H.

The term "FR-1-NP-1" as used herein refers to a compound of Formula I, wherein $R^a$ is H and NP is a peptide of the sequence:

[SEQ ID NO: 27]
Glu-Trp-Asp-Leu-Val-Gly-Ile-Pro-Gly-Lys-Arg-Ser-
Glu-Arg-Phe-Tyr.

The term "FR-2-NP-1" as used herein refers to a compound of Formula I, wherein $R^a$ is H and NP is a peptide of the sequence:

[SEQ ID NO: 28]
Ile-Pro-Gly-Lys-Arg-Ser-Glu-Arg-Phe-Tyr.

The term "FR-3-NP-1" as used herein refers to a compound of

Formula I, wherein $R^a$ is H and NP is a peptide of the sequence:

[SEQ ID NO: 12]
Ser-Glu-Arg-Phe-Tyr-Glu-Cys-Cys-Lys-Glu.

The terms "FR-1-NP-1-KLH", "FR-2-NP-1-KLH" and "FR-3-NP-1-KLH" as used herein refer to peptides "FR-1-NP-1", "FR-2-NP-1" and "FR-3-NP-1", respectively, conjugated to KLH (keyhole limpet hemocyanin).

The term (R-2-FR-3-NP-1)$_2$-Lys-OH refers to a compound of the Formula I:

$$[R^a\text{-NP}]_m\text{-}L_p \qquad (I),$$

wherein NP is FR-3-NP-1 [SEQ ID No:12], m is 2, p is 1, L is a linker group of the formula:

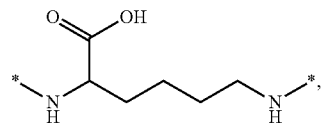

where * represents the site of attachment to the two NP groups and $R^a$ is a group of the formula:

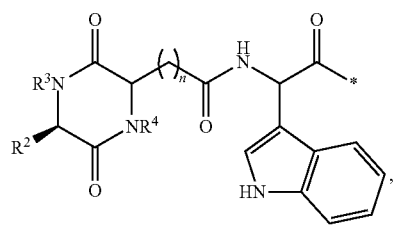

wherein * represents the site of attachment to NP, n is 1, $R^2$ is $CH_3$, and $R^3$ and $R^4$ are both H.

The term (FR-3-NP-1)$_2$-Lys-OH refers to a compound of the Formula:

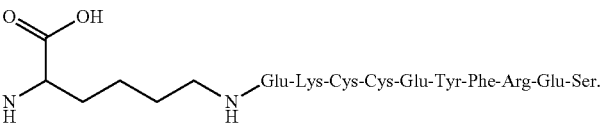

II. Compounds and Compositions of the Application

Compounds of the application were studied in mice with an experimentally induced form of Alzheimer's disease (AD) to investigate the compounds' ability to stimulate protective immunity without conjugation to a carrier protein and without the use of complete Freund's adjuvant. For an experimental model of Alzheimer's disease, bulbectomized mice were used (NMRI mice that have undergone bulbectomy—removal of the olfactory bulb—and consequently develop signs of Alzheimer's-like neurodegenerative process; the experiment is described in detail in Kamynina et al., Vaccination with peptide 173-193 of acetylcholine receptor α7-subunit prevents memory loss in olfactory bulbectomized mice; Journal of Alzheimer's Disease, 2010; 21(1):249-61.). Mice of the NMRI strain are commercially available, and can be obtained, for example, from Charles River Laboratories. Immunization of mice was performed by the compounds: NP-1, R-1-NP-1, (FR-3-NP-1)$_2$-Lys-OH and (R-2-FR-3-NP-1)$_2$-Lys-OH. Based on prior research, a four-time immunization scheme was used; peptides were administered in conjunction with incomplete Freund's adjuvant (IFA). The bulbectomy operation was performed between the second and third immunization. After the fourth immunization (one month after the bulbectomy), tests of animals' spatial memory were performed, followed by their slaughter and collection of blood serum and brain structures to determine the level of β-amyloid. The study produced the following findings:
(1) Immunization of mice by R-1-NP-1 and (R-2-FR-3-NP-1)₂-Lys-OH in conjunction with IFA led to memory protection after bulbectomy, in contrast to identical immunization scheme by NP-1 and (R-2-FR-3-NP-1)₂-Lys-OH with IFA, which did not exhibit memory protection of bulbectomized animals.
(2) Both R-1-NP-1 and NP-1 stimulated the formation of a similar level of antipeptide antibodies in the blood serum of the animals.
(3) Immunization with peptides NP-1 and R-1-NP-1 causes a significant reduction of β-amyloid in the brain of bulbectomized animals compared to non-immunized bulbectomized mice (control).

These results suggest that compounds of the application, including R-1-NP-1 and (R-2-FR-3-NP-1)₂-Lys-OH, cause induction of antipeptide antibodies without conjugation to a carrier protein, and without the use of complete Freund's adjuvant. Administration of R-1-NP-1 and (R-2-FR-3-NP-1)₂-Lys-OH into test subjects was followed by memory protection effects in bulbectomized animals, which correlates with decreased levels of β-amyloid in the brains of the animals.

The novel compounds R-1-NP-1 and (R-2-FR-3-NP-1)₂-Lys-OH has been prepared. These compound comprises a peptide with the sequence Glu-Trp-Asp-Leu-Val-Gly-Ile-Pro-Gly-Lys-Arg-Ser-Glu-Arg-Phe-Tyr-Glu-Cys-Cys-Lys-Glu [SEQ ID NO:1], and a fragment of NP-1, Ser-Glu-Arg-Phe-Tyr-Glu-Cys-Cys-Lys-Glu [SEQ ID NO:12] covalently linked (built-in) to an immunoactive adjuvant. Further, it has been demonstrated herein that certain peptide fragments of NP-1 conjugated to KLH are capable of preserving spatial memory in bulbectomized mice immunized with the peptide fragment-KLH conjugate.

Accordingly, the present application includes a compound of Formula I:

$$[R^a\text{-}NP]_m\text{-}L_p \qquad (I)$$

wherein
NP is a sequence comprising at least 9 contiguous amino acids of Glu-Trp-Asp-Leu-Val-Gly-Ile-Pro-Gly-Lys-Arg-Ser-Glu-Arg-Phe-Tyr-Glu-Cys-Cys-Lys-Glu [SEQ ID NO:1], optionally with conservative amino acid substitutions or amino acid analog substitutions thereof, or
NP is a deletion or addition analog of [SEQ ID NO:1], optionally with conservative amino acid substitutions or amino acid analog substitutions thereof;
m is 1 or 2;
p is 0 when m is 1 and p is 1 when m is 2;
L is a linker group;
$R^a$ is H or a group of the formula:

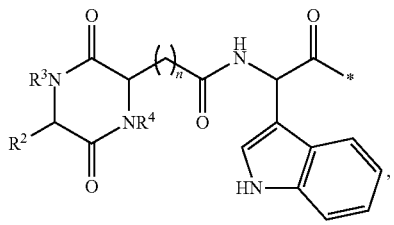

wherein
* represents the site of attachment to NP;
n is 1 or 2;
$R^2$ is $C_{1-6}$alkyl or $C_{1-3}$alkylenePh; and
$R^3$ and $R^4$ are independently selected from H and $C_{1-4}$alkyl,
provided that when $R^a$ is H and m is 1, NP is not [SEQ ID NO:1],
or pharmaceutically acceptable salts thereof.

In an embodiment of the application, NP is selected from:

| | |
|---|---|
| EWDLVGIPGKRSERFYECCKE; | [SEQ ID NO: 1] |
| WDLVGIPGKRSERFYECCKE; | [SEQ ID NO: 2] |
| DLVGIPGKRSERFYECCKE; | [SEQ ID NO: 3] |
| LVGIPGKRSERFYECCKE; | [SEQ ID NO: 4] |
| VGIPGKRSERFYECCKE; | [SEQ ID NO: 5] |
| GIPGKRSERFYECCKE; | [SEQ ID NO: 6] |
| IPGKRSERFYECCKE; | [SEQ ID NO: 7] |
| PGKRSERFYECCKE; | [SEQ ID NO: 8] |
| GKRSERFYECCKE; | [SEQ ID NO: 9] |
| KRSERFYECCKE; | [SEQ ID NO: 10] |
| RSERFYECCKE; | [SEQ ID NO: 11] |
| SERFYECCKE; | [SEQ ID NO: 12] |
| ERFYECCKE; | [SEQ ID NO: 13] |
| EWDLVGIPGKRSERFYECCK; | [SEQ ID NO: 14] |
| EWDLVGIPGKRSERFYECC; | [SEQ ID NO: 15] |
| EWDLVGIPGKRSERFYEC; | [SEQ ID NO: 16] |
| EWDLVGIPGKRSERFYE; | [SEQ ID NO: 17] |
| EWDLVGIPGKRSERFY; | [SEQ ID NO: 18] |
| EWDLVGIPGKRSERF; | [SEQ ID NO: 19] |
| EWDLVGIPGKRSER; | [SEQ ID NO: 20] |
| EWDLVGIPGKRSE; | [SEQ ID NO: 21] |
| EWDLVGIPGKRS; | [SEQ ID NO: 22] |

```
EWDLVGIPGKR;                    [SEQ ID NO: 23]

EWDLVGIPGK;                     [SEQ ID NO: 24]

EWDLVGIPG;                      [SEQ ID NO: 25]

WDLVGIPGK;                      [SEQ ID NO: 26]

EWDLVGIPGKRSERFY;               [SEQ ID NO: 27]
and

IPGKRSERFY,                     [SEQ ID NO: 28]
``` and conservative amino acid substitutions thereof.

In an embodiment NP, is NP-1 [SEQ ID NO:1] or FR-3-NP-1 [SEQ ID NO:12].

In an embodiment, m is 2 and L is an amino acid in which one $R^a$-NP group is attached at the amino position and another $R^a$-NP group is attached to a functional group in the side chain. In a further embodiment, L is lysine, serine, threonine, aspartic acid or glutamic acid. In a further embodiment, L is lysine. In another embodiment, L is a di-amino or di-hydroxy $C_{1-20}$alkylene.

In an embodiment, $R^a$ is H, m is 1 and L is not present.

In another embodiment, $R^a$ is a group of the formula:

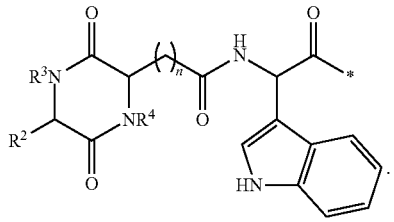

In another embodiment, $R^a$ is a group of the formula:

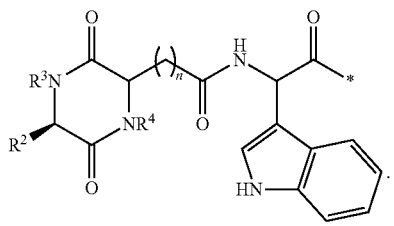

In another embodiment, n is 1 or 2.

In an embodiment, $R^2$ is $C_{1-6}$alkyl or CH$_2$Ph. In a further embodiment, $R^2$ is CH$_3$, CH(CH$_3$)$_2$, CH$_2$CH(CH$_3$)$_2$, CH(CH$_3$)(CH$_2$CH$_3$) or CH$_2$Ph. In a further embodiment, $R^2$ is CH$_3$.

In an embodiment, $R^3$ and $R^4$ are independently selected from H and CH$_3$. In a further embodiment, $R^3$ and $R^4$ are both H.

In an embodiment, the stereochemistry of all amino acids in the compound of Formula I is the natural, or L, configuration.

It is an embodiment that the compound of Formula I is selected from R-1-NP-1, FR-1-NP-1, FR-2-NP-1, FR-3-NP-1, [R-2-NP-1]$_2$-Lys-OH, [R-2-FR-1-NP-1]$_2$-Lys-OH, [R-2-FR-2-NP-1]$_2$-Lys-OH and [R-2-FR-3-NP-1]$_2$-Lys-OH. In another embodiment, the compound of Formula I is R-1-NP-1. In another embodiment, the compound of Formula I is [R-2-FR-3-NP-1]$_2$-Lys-OH.

In an embodiment of the present application, m is 1 and L is not present (p is 0), and the compound of Formula I is:

$$R^a\text{-NP} \qquad \qquad I,$$

wherein

NP is a sequence comprising at least 9 contiguous amino acids of Glu-Trp-Asp-Leu-Val-Gly-Ile-Pro-Gly-Lys-Arg-Ser-Glu-Arg-Phe-Tyr-Glu-Cys-Cys-Lys-Glu [SEQ ID NO:1], optionally with conservative amino acid substitutions or amino acid analog substitutions thereof, or NP is a deletion or addition analog of [SEQ ID NO:1], optionally with conservative amino acid substitutions or amino acid analog substitutions thereof; and $R^a$ is H or a group of the formula:

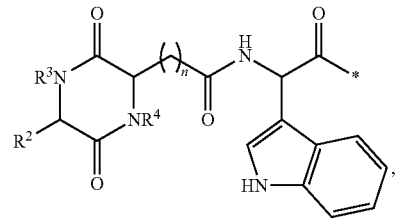

wherein

* represents the site of attachment to NP;
n is 1 or 2;
$R^2$ is $C_{1-6}$alkyl or $C_{1-3}$alkylenePh; and
$R^3$ and $R^4$ are independently selected from H and $C_{1-4}$alkyl,
provided that when $R^3$ is H, NP is not [SEQ ID NO:1],
or pharmaceutically acceptable salts thereof.

It is a further embodiment that the compound of Formula I is conjugated to a protein carrier such as KLH or BSA. It is an embodiment that the protein carrier is KLH.

Also included within the compounds of the application are the NP fragments themselves. Accordingly, the present application also includes a compound selected from:

```
WDLVGIPGKRSERFYECCKE;           [SEQ ID NO: 2]

DLVGIPGKRSERFYECCKE;            [SEQ ID NO: 3]

LVGIPGKRSERFYECCKE;             [SEQ ID NO: 4]

VGIPGKRSERFYECCKE;              [SEQ ID NO: 5]

GIPGKRSERFYECCKE;               [SEQ ID NO: 6]

IPGKRSERFYECCKE;                [SEQ ID NO: 7]

PGKRSERFYECCKE;                 [SEQ ID NO: 8]

GKRSERFYECCKE;                  [SEQ ID NO: 9]
```

KRSERFYECCKE; [SEQ ID NO: 10]

RSERFYECCKE; [SEQ ID NO: 11]

SERFYECCKE; [SEQ ID NO: 12]

ERFYECCKE; [SEQ ID NO: 13]

EWDLVGIPGKRSERFYECCK; [SEQ ID NO: 14]

EWDLVGIPGKRSERFYECC; [SEQ ID NO: 15]

EWDLVGIPGKRSERFYEC; [SEQ ID NO: 16]

EWDLVGIPGKRSERFYE; [SEQ ID NO: 17]

EWDLVGIPGKRSERFY; [SEQ ID NO: 18]

EWDLVGIPGKRSERF; [SEQ ID NO: 19]

EWDLVGIPGKRSER; [SEQ ID NO: 20]

EWDLVGIPGKRSE; [SEQ ID NO: 21]

EWDLVGIPGKRS; [SEQ ID NO: 22]

EWDLVGIPGKR; [SEQ ID NO: 23]

EWDLVGIPGK; [SEQ ID NO: 24]

EWDLVGIPG; [SEQ ID NO: 25]

WDLVGIPGK; [SEQ ID NO: 26]

EWDLVGIPGKRSERFY; [SEQ ID NO: 27]
and

IPGKRSERFY, [SEQ ID NO: 28]

or any one [SEQ ID NO:2] to [SEQ ID NO: 28] in which one or more of the amino acids has been substituted with a conservative amino acid analog thereof, or pharmaceutically acceptable salts thereof.

In an embodiment of the application, the compound is SERFYECCKE [SEQ ID NO: 12], or [SEQ ID NO:12] in which one or more of the amino acids has been substituted with a conservative amino acid analog thereof, or a pharmaceutically acceptable salt thereof.

The compounds of the application also include any one [SEQ ID NO:2] to [SEQ ID NO: 28], for example, SERFYECCKE [SEQ ID NO: 12], conjugated to a protein carrier such as KLH or BSA. It is an embodiment that the protein carrier is KLH.

The present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier.

In an embodiment, the composition further comprises an adjuvant. It is an embodiment that the adjuvant is incomplete Freund's adjuvant.

The compounds of the application may be administered to a subject in a variety of forms depending on the selected route of administration, as will be understood by those skilled in the art. A compound of the application may be administered, for example, by oral, parenteral, buccal, sublingual, nasal, rectal, patch, pump or transdermal administration and the pharmaceutical compositions formulated accordingly.

Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

A compound of the application may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines.

It is also possible to freeze-dry the compounds of the application and use the lyophilizates obtained, for example, for the preparation of products for injection.

A compound of the application may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compounds of the application may also be coupled with soluble polymers as targetable drug carriers. Such polymers can include polyvinylpyrrolidone, pyran copolymer, polyhydroxypropylmethacrylamide-phenol, polyhydroxy-ethyl-aspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Compounds of the application may be used alone or in combination with other known agents useful for treating diseases, disorders or conditions characterized by or associated with β-amyloid accumulation. When used in combination with other agents useful in treating diseases, disorders or conditions characterized by or associated with β-amyloid accumulation, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of compounds of the application can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. In an embodiment of the application, compositions formulated for oral administration and the compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. Compounds of the application may be administered in a single daily dose or the total daily dose may be divided into two, three or four daily doses.

III. Methods and Uses of the Application

The compounds of the application have been shown to be capable of stimulating antibody formation and reducing levels of β-amyloid in bulbectomized mice. In view of this, the compounds of the application are useful for treating diseases, disorders or conditions that are characterized by or associated with β-amyloid accumulation.

Therefore the compounds of the present application are useful as medicaments. Accordingly, the present application includes a compound of the application for use as a medicament.

The present application also includes a method of treating diseases, disorders or conditions that are characterized by or associated with β-amyloid accumulation comprising administering a therapeutically effective amount of one or more compounds of the application to a subject in need thereof.

The present application further includes a use of one or more compounds of the application for treating diseases, disorders or conditions characterized by or associated with β-amyloid accumulation as well as a use of one or more compounds of the application for the preparation of a medicament for treating diseases, disorders or conditions characterized by or associated with β-amyloid accumulation. Finally, the application also includes one or more compounds of the application for use in treating diseases, disorders or conditions characterized by or associated with β-amyloid accumulation.

In embodiments of the application, the diseases, disorders or conditions characterized by or associated with β-amyloid accumulation include Alzheimer's disease, Down syndrome, transient cerebral ischemia, HIV infection, traumatic brain injury, cerebral cortical infarction and chronic traumatic encephalopathy. As mentioned above, compounds of the application have been demonstrated to be capable of preserving spatial memory in bulbectomized mice. Accordingly, it is an embodiment of the application that the disease, disorder or condition characterized by or associated with β-amyloid accumulation is Alzheimer's disease.

The following non-limiting examples are illustrative of the present application:

EXAMPLES

Example 1

Immunization of Mice with Compounds NP-1 and R-1-NP-1

Materials and Methods

I. Preparation of NP-1 and R-1-NP-1

Peptide Synthesis

All the peptides were synthesized by the solid-phase Fmoc-chemistry using Wang resin with molar capacity of hydroxyl groups 0.37 mmol/g. Cleavage of peptides from the resin was carried out in a mixture containing trifluoroacetic acid (95%), triisopropylsilane (2.5%), and water (5%) (3 ml) for 2 h.

The peptides were purified by reversed phase HPLC on Jupiter columns 18 μ C18 300A, 250×10 mm (Phenomenex, USA). The homogeneity of the synthesized peptides was estimated by reverse-phase HLPC chromatography on Jupiter columns 5 μ C18 300A, 250×4.6 mm (Phenomenex, USA).

Amino-acid analysis was carried out on Biotronik LC-3000 (Germany) and MALDI mass spectrometry on a VISION 2000 instrument (Bioanalysis, UK). Purity of the peptides obtained was estimated as >95%. Table 1 shows the analytical data for R-1-NP-1, and Table 2 shows the analytical results for R-1-NP-1.

II. Mouse Experimental Model

Experiments were performed on NMRI mice weighing 20-30 g. Initiation of Alzheimer's type neurodegenerative process was caused by the removal of the animal's olfactory bulb (bulbectomy). The operation was performed under sterile conditions under nembutal anesthesia (40 mg/kg). For local anaesthesia during scalping, a subcutaneous injection of 0.5% solution of novocaine was used. Bilateral removal of the olfactory bulbs was performed by aspiration through a burr hole in the skull coordinates: AP −3.5; L 0 (Rosen G D, Williams A G, Capra J A, Connolly M T, Cruz B, Lu L, Airey D C, Kulkami K, Williams R W (2000) The Mouse Brain Library@www.mbl.org. Int Mouse Genome Conference 14: 166. www.mbl.org.). A group of animals to serve as control was sham-operated (SO); these animals were subjected to the same procedure but without removal of the olfactory bulbs. After surgery all animals were injected with "Bitsillin 5" antibiotic into the muscles of the hind paw at a dose of 6000 units for the prevention of infection. Upon completion of behavioral experiments, morphological studies of animal brains were conducted to ensure complete removal of olfactory bulbs.

III. Immunization of Mice

To study the immunogenic activity, immunization of four different strains of mice with compounds NP-1 and R-1-NP-1 was performed. Three different schemes of immunization were used: without the use of an adjuvant, with incomplete Freund's adjuvant, and with complete Freund's adjuvant.

Mice were injected with the vaccination complex into the base of their tails according to the schedule shown in Table 3. The immunization was carried out in four stages. The peptides were dissolved in saline and mixed with an equal volume of incomplete Freund's adjuvant (IFA) to obtain an emulsion. The emulsion was injected subcutaneously into the base of the tail in a volume of 0.2 ml at the rate of 100 μg (for the first immunization) and 50 μg of peptide (in the second, third and fourth immunizations) per mouse. Immunization compounds were used with 25% excess to compensate for unavoidable losses when working with small volumes of emulsions.

IV. Assessment of Spatial Memory

The state of spatial memory was assessed after mice had developed spatial skills in the Morris water maze, which combines training in the formation of active avoidance and the ability to navigate in space. This method enables separate evaluation of learning and memory.

The experimental chamber was a plastic pool of dimensions 100×60×30 cm, filled with water at a temperature of 23 degrees Celsius. The basin area was divided into four equal sectors, one of which had a rescue platform 5 cm in diameter, immersed in 0.5 cm of water. The water was clouded with milk so that animals could not visually detect the rescue platform.

All mice were pre-tested for the ability to swim and absence of an original sector preference in the water maze. The goal of the education was to have mice in one minute find the underwater platform and remember its location. Training was conducted in four sessions every day for five days, and the latency period for finding the platform was recorded for every session. 24 hours after completion of training, the level of the animal's spatial memory in the absence of a rescue platform was tested for one minute. Two indicators were used in analyzing the results: the number of visits to each sector of the maze and time spent in each sector.

Two-factor analysis (general ANOVA) was used for statistical analysis of behavioral data. Post-hoc analysis was performed using the criterion of LSD (least significant difference). The reliability of the results was also evaluated using two-tailed Student's t-test.

V. Blood Collection and Preparation of Serum

For the blood collection and preparation of serum for further studies in enzyme immunoassay (EIA), a day after the test of spatial memory, the mice received a lethal dose of Nembutal (60 mg/kg), after which they had their chest opened. Blood was collected by syringe from the right ventricle of the heart into individual plastic tubes. The volume collected was at least 500 μl. After this, transcardial perfusion was carried out by chilled saline solution (isotonic saline for injection) in a volume of 10 ml. Tubes of selected blood were kept for 1 hour in an oven at 37° C. Then, centrifugation was performed at 2500 rev/min for 10 min, the supernatant were collected and transferred to clean labeled tubes. The volume of the obtained sera was 50-150 μl. For pool preparation 10 μl of individual sera were mixed. Serum was stored at −18° C.

VI. Collection of Brain Structures

To collect brain structures to determine the biochemical level of β-amyloid, mice were decapitated and the brain was removed in the cold. The cortex was removed by scalpel from both hemispheres, the hippocampus was bilaterally removed, the probes were placed in labeled plastic test tubes that were frozen at −80° C. and stored in a freezer until the biochemical study of the level of β-amyloid.

VII. Enzyme Immunoassay for β-Amyloid

Biochemical identification of β-amyloid (1-40) by enzyme immunoassay was performed as follows: samples of the cortex and hippocampus, which were stored at −80° C. after collection, were weighed, thawed at room temperature, and then homogenized in a solution of 2% CHAPS 20 mM Tris-HCl (pH 7.7) in the presence of protease inhibitors (10 μg/ml leupeptin, 10 μg/ml aprotinin and 10 μg/ml AEBSF)

in a volume calculated for each sample (4 ml of solution per 1 g of tissue), using a RT-12 tissue microgrinder in a glass beaker for the homogenization using a ground-glass pestle. Homogenates were centrifuged at 21,000 g at 4° C. for 30 min. Selected supernatants were stored at −80° C. and thawed immediately prior to the immunoassay analysis.

Another part of the samples were homogenized in 5 M guanidine-HCl solution of 50 mM Tris-HCl (pH 8.0), in a volume calculated for each sample (400 mcl of solution per 50 mg of tissue). The samples were stirred for 3-4 hours at room temperature, then diluted in BSAT-DPBS (5% BSA, 0.03% Tween-20) buffer, centrifuged at 21,000 g at 4° C. for 30 min, after which the supernatants were collected.

The immunosorbent assay was performed using the instructions on the ELISA for the determination of β-amyloid (1-40) (Aβ40) mouse (ELISA kit mouse Aβ40, Invitrogen).

Results and Discussion

I. Spatial Memory

Tables 4 and 5 show the results of data processing of the spatial memory test using univariate analysis (one-way ANOVA), which allows to judge the ability of the animal to discriminate between different sections of the Morris water maze.

The data presented in Tables 4 and 5 show that the sham-operated (SO) animals and SO animals immunized with NP-1 and R-1-NP-1 had high preference for training sector (sector 3 containing the platform during training), both by time spent and by relative number of visits. Unvaccinated bulbectomized (BE) mice and BE animals immunized with NP-1 were not capable of recalling the training sector during the spatial memory tests, as evidenced by low values of F for these groups. Low p-values of time spent in training sector (Table 4) in non-immunized BE mice points to severe memory impairment in this group of animals. A much higher value of F in the group of BE animals immunized with the R-1-NP-1 indicates the ability of these mice to differentiate various sectors of the maze and to recall the compartment in which the rescue platform was located during training. Results of post-hoc analysis are presented in FIGS. 1 (A, B) and 2 (A, B).

Immunization of FO mice with NP-1 and R-1-NP-1 did not adversely affect their spatial memory as tested in the Morris water maze (FIGS. 1 A and B). Immunized FO animals, as well as control FO animals had selected the training sector (sector 3 containing the platform during training) with high statistical significance, indicated by both time spent (FIG. 1 A), and the number of visits (FIG. 1 B).

In the tests of spatial memory, BE mice immunized with NP-1 peptide did not improve their memory and did not single out the sector in which the rescue platform was during training, which indicates significant impairment in the processes of memorization and reproduction of developed skills.

Figure 2:
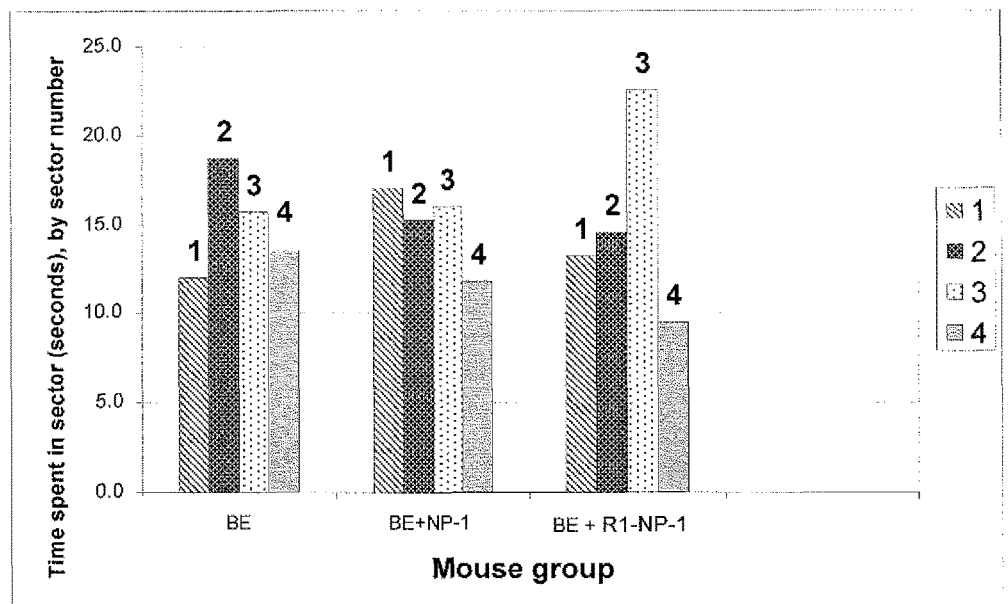
FIG. 2 shows the effect of immunization with NP-1 and R-1-NP-1 on the spatial memory of bulbectomized (BE) mice: (A) data by time spent in the sectors of a Morris water maze; (B) data by relative number of sector visits, expressed as a percentage relative to the total number of all sector visits (calculated individually for each animal then aggregated for the group. Sector 3 contained the rescue platform during training.
Figure 2:
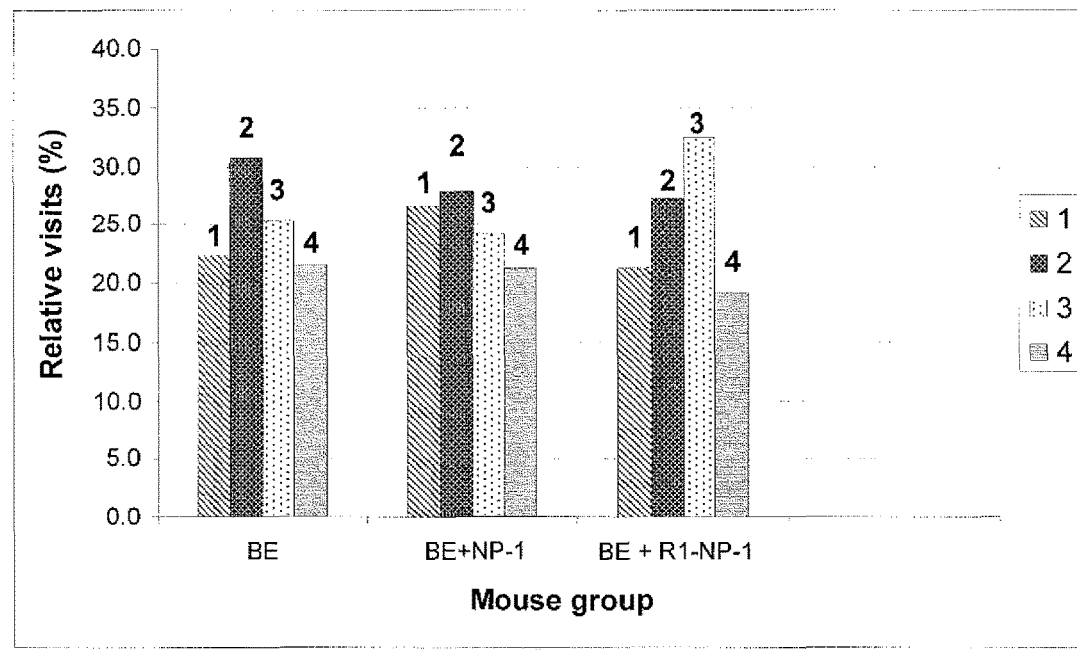

In contrast, BE mice immunized with peptide R-1-NP-1 showed improvement of spatial memory. These animals were able to single out the training sector, as indicated by both time spent (FIG. 2 A), and the number of visits (FIG. 2 B).

Thus, immunization by R-1-NP-1 resulted in improved memory in BE animals, while the NP-1 peptide in the absence of complete Freund's adjuvant did not show protective activity in BE mice. It is important to note that none of the compounds used for immunization negatively impacted the memory of FO animals, indicating the absence of adverse memory-related side effects of such immunization.

II. Analysis of Sera

The results of studying the sera of sham-operated (SO) and bulbectomized (BE) mice of the NMRI strain, immunized with NP-1 and R-1-NP-1 in IFA are shown in Tables 6-9. Tables 6-9 show the antibody titers in individual sera and pools of sera, expressed as -Ig serum dilution.

III. Determination of β-Amyloid Levels in the Brain of BE Mice Immunized with NP-1 and R-1-NP-1

Figure 3:
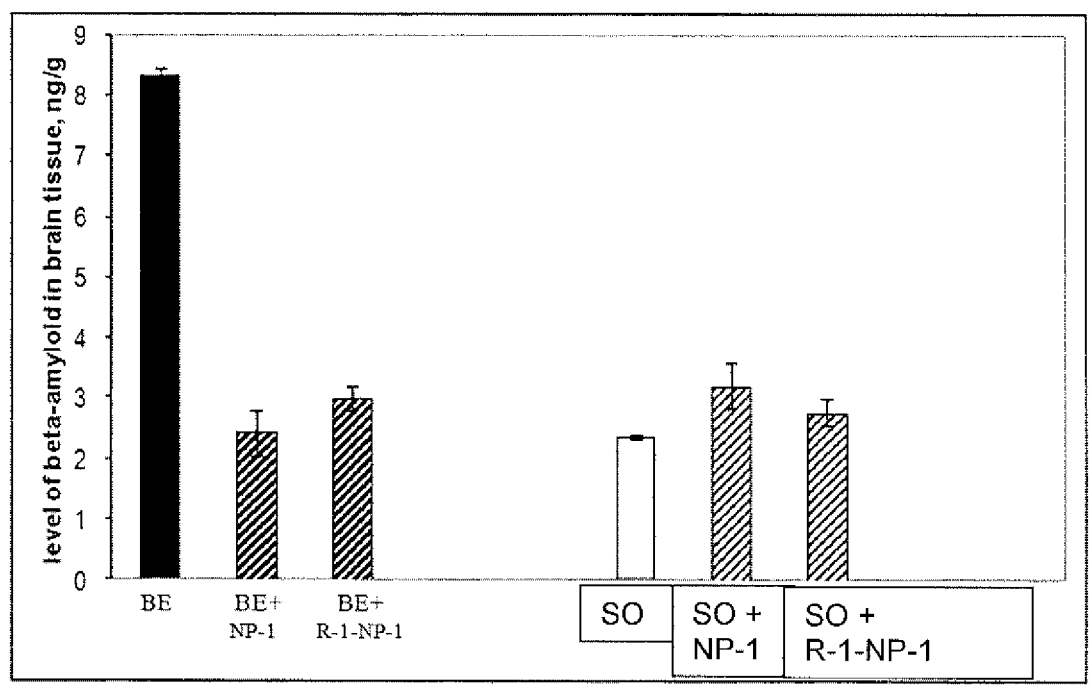
FIG. 3 shows data on the levels of βA in the brain (cortex+hippocampus) of mice immunized with peptides NP-1 and R-1-NP-1.

After testing the memory of all groups of animals, brain perfusion was carried out in the cold under deep anaesthesia, and individual samples of brain tissue (cortex+hippocampus) were collected, which were stored in a freezer at a temperature of −80° C. until biochemical studies. The method of extraction of β-amyloid from the brain tissue and procedure to determine the enzyme immunoassay ELISA is described in detail in Kamynina et al., Vaccination with peptide 173-193 of acetylcholine receptor α7-subunit prevents memory loss in olfactory bulbectomized mice; Journal of Alzheimer's Disease, 2010; 21(1):249-61. The data obtained are presented in Table 10 and FIG. 3.

The presented data suggest that, as expected, the level of β-amyloid in the brain BE animals was significantly higher than the FO animals, by 353.8%. Immunization of FO animals by all of the peptides did not lead to significant changes in the concentration of β-amyloid in their brains (the concentration of β-amyloid in the FO groups of animals immunized with peptides NP-1 and R-1-NP-1 did not differ from its level in non-immunized control mice, FO, although it is possible to note some, albeit statistically insignificant, trend to its increase). All of BE animals immunized with the peptides studied were characterized by significantly reduced content of β-amyloid in brain tissue as compared to non-immunized BE animals.

Thus, both investigated compounds appear capable of stimulating antibody formation in experimental animals and reducing levels of β-amyloid, but immunization by compound R-1-NP-1 protects the spatial memory of animals with experimentally induced form of Alzheimer's disease.

Example 2

Immunization of Mice with Fragments of NP-1

In Example 1, it was shown that immunization with a synthetic fragment of the α-7 acetylcholine receptor subunit (NP-1) causes the formation of antibodies that protect neurons from death, reducing the level of β-amyloid in the brain and protecting the spatial memory of animals with experimentally induced form of Alzheimer's disease. To identify shorter peptide sequences in NP-1 exhibiting immunoprotective activity, truncated forms of NP-1 were designed, synthesized and in vivo studies were performed.

NMRI mice (see Example 1) were immunized with peptides conjugated to snail keyhole limpet hemocyanin (KLH).

In this study, a scheme with a double introduction of peptides into mice with complete Freund's adjuvant (CFA) for the first immunization and incomplete Freund's adjuvant (IFA) for the second immunization was used. Between the first and second immunization a bulbectomy was performed. After the second immunization, one month after bulbectomy, the mice's state of spatial memory was tested, after which the mice were put down and their blood and cerebrospinal fluid were collected to determine their level of antipeptide antibodies.

The peptide fragments of NP-1 that were used are as follows:

```
173-188 (FR-1-NP-1) of the sequence
                                   [SEQ ID NO: 27]
Glu-Trp-Asp-Leu-Val-Gly-Ile-Pro-Gly-Lys-Arg-Ser- Glu-Arg-Phe-Tyr, 179-188 (FR-2-NP-1) of the sequence
                                   [SEQ ID NO: 28]
Ile-Pro-Gly-Lys-Arg-Ser-Glu-Arg-Phe-Tyr,
and 184-193 (FR-3-NP-1)
                                   [SEQ ID NO: 12]
Ser-Glu-Arg-Phe-Tyr-Glu-Cys-Cys-Lys-Glu-OH.
```

To prepare the peptide conjugates with KLH, 0.75 mg of peptide was dissolved in 0.65 ml of KLH in PBS with a protein concentration of 5.8 mg/ml and stirred for an hour while adding 38 µl of 2.5% glutaraldehyde solution in PBS. The resulting solution was stirred for 15 hours and dialyzed against PBS for 20 hours.

NMRI mice were immunized according to the schedule provided in Table 11.

It was determined that in the group of sham-operated (SO) mice (control group on which bulbectomy was not performed), all mice were successfully educated (100%). None of the non-immunized bulbectomized (BE) mice were successfully educated. Bulbectomized mice that were immunized with FR-1-NP-1-KLH and FR-2-NP-1-KLH exhibited spatial memory preservation in 75% of the animals. The BE group immunized with FR-3-NP-1-KLH was successfully educated in its entirety (100% of the animals).

Tables 12 and 13 present the results of statistical analysis of spatial memory test data using univariate analysis (one-way ANOVA), to judge the ability of the animal to distinguish sections of the Morris water maze.

The data presented in Tables 12 and 13 show that the sham-operated (SO) animals had high preference for the training sector (sector 3 containing the platform during training), both by time spent and by relative number of visits. Non-immunized BE mice were not capable of recalling the training sector during the spatial memory tests, as evidenced by low values of F for these groups. Low p-values of time spent in training sector (Table 12) in non-immunized BE mice point to severe memory impairment in this group of animals. A much higher value of F in the group of BE animals immunized with the FR-1-NP-1-KLH; FR-2-NP-1-KLH, and FR-3-NP-1-KLH suggests an increasing ability of these mice to differentiate various sectors of the maze and to recall the compartment in which the rescue platform was located during training.

The data presented in Table 12 show that out of all BE groups, the mice immunized with FR-3-NP-1-KLH had the best spatial memory preservation, which was manifested in more time spent by these animals in the training sector as compared to other BE groups.

Table 13 shows that for these groups of mice, the ratio of entries into the compartments of the maze changed to a lesser extent under the influence of immunization, as indicated by the lack of statistical significance in isolating the training sector by all immunized mice. However, it should be noted that only the BE group immunized with FR-3-NP-1-KLH exhibited preference for the training sector, although statistical significance of differentiation from other sectors was not achieved because of the wide variance of experimental data.

To evaluate the spatial memory test results obtained in the Morris water maze, researchers often compare groups using only the data obtained for the training sector. Employing this method, arranged in descending order, the values of time spent in the training sector by various groups were as follows:

FO>BE+FR-3-NP-1-KLH>BE+FR-2-NP-1-KLH>BE+FR-1-NP-1-KLH>BE ($30.0\pm2.31$ sec>$25.25\pm3.47$ sec>$20.1\pm1.86$ sec>$18.33\pm2.04$ sec>$15.44\pm1.49$ sec, respectively).

The above comparison shows that non-immunized BE mice and BE mice immunized with peptides FR-2-NP-1-KLH and FR-1-NP-1-KLH were not significantly different from each other in terms of time spent in the training compartment, while the BE group immunized with FR-3-NP-1-KLH had a much greater value of this parameter, almost in line with the FO group.

A similar analysis performed with another indicator of the behavior of animals in the Morris water maze—the ratio of the number of entries into the training sector—gave the following results. Sorting groups in the decreasing order of the ratio of entries into the training sector provides the following trend:

FO>BE+FR-2-NP-1-KLH>BE+FR-3-NP-1-KLH>BE+FR-1-NP-1-KLH ($40.44\pm2.15\%$ > $35.5\pm2.64\%$ > $32.0\pm4.3\%$ > $30.83\pm2.32\%$ > $27.22\pm2.36\%$, respectively).

The data show that for this indicator the BE groups immunized with various truncated fragments of NP-1 did not significantly differ from each other.

In conclusion, as a result of these studies, it has been established that fragment FR-3-NP-1-KLH (184-193) appears to have the strongest memory protection effect in BE mice, as indicated by time spent in the training sector. Based on years of experience with the present methodology for assessing the spatial memory in the Morris water maze, it was known that animals tend to differ in their strategy of locating the training sector. That is why two measures were analyzed—time spent in the training sector and the ratio of visits to the training sector. A preference for the training sector exhibited by mice according to at least one of the above measures is known to indicate adequate presence of spatial memory in those animals.

Example 3

Immunization of Mice with Compounds (FR-3-NP-1)$_2$-Lys-OH and (R-2-FR-3-NP-1)$_2$-Lys-OH The objective of this study was to investigate the ability of the compounds (FR-3-NP-1)$_2$-Lys-OH and (R-2-FR-3-NP-1)$_2$-Lys-OH to protect the spatial memory of the bulbectomized mice upon four-time immunization with FIA. The active compounds will be immunogenic structures, which do not require the use of KLH and Freund's complete adjuvant (FCA) to provide a protective effect in a murine model.

I. Study Description

Mice were immunized with two compounds: (R-2-FR-3-NP-1)2-Lys-OH and (FR-3-NP-1)2-Lys-OH, four times using IFA. After the second immunization, the animals had their olfactory bulbs extracted (underwent bulbectomy). At the end of the immunization period, the mice were trained in the Morris water maze and then tested for skill preservation (which determined the level of spatial memory).

II. Synthesis of Peptides

(a) Synthesis of (FR-3-NP-1)$_2$-Lys-OH

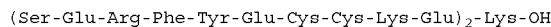
(Ser-Glu-Arg-Phe-Tyr-Glu-Cys-Cys-Lys-Glu)$_2$-Lys-OH (FR-3-NP-1)$_2$-Lys-OH is comprised of two oligopeptides FR-3-NP-1, coupled to the α- and ε-aminogroups of the Lys side chain. Synthesis was done in an automated solid state peptide synthesizer Syro™ I, starting with 100 mg of 4-(hydroxymethyl)phenyloxymethyl-polystyrol (Wang polymer) and using 3-fold excess of amino acids for each step coupling, without acetylation of unreacted amine groups. Elongation of the peptide chain was carried out in accordance with the protocol of the synthesizer's software package SyroXP™ Peptide. After synthesis the peptidyl-polymer was filtered and dried in air. The dried peptidyl-polymer was then deblocked.

Preparation of Target Peptide (Ser-Glu-Arg-Phe-Tyr-Glu-Cys-Cys-Lys-Glu)$_2$-Lys-OH.

The dried peptidyl-polymer was transferred to a flask, to which then was added 3±0.1 ml of deblocking mixture: trifluoroacetic acid, thioanisole, phenol, water, ethanedithiol, triisopropylsilane in volumetric ratio 81.5/5/5/5/2.5/1 and stirred for 2 hours. The polymer was then filtered, and the solution was evaporated using a rotary evaporator. To the residue was added 20±1 ml of dry diethyl ether, transferred to a glass filter and filtered. The precipitate of crude peptide was washed by 20±1 ml of diethyl ether and dried in air.

Chromatographic Purification of (FR-3-NP-1)$_2$-Lys-OH

Purification was performed by reversed-phase high performance liquid chromatography (HPLC) using Phenomenex column 250×4.6 mm, sorbent Jupiter 5 μ C18 300 Å, eluent flow rate 1 ml/min. Gradient of acetonitrile in 0.1% TFA from 10% to 70% in 60 minutes. Speed 1 ml/min, t=20° C. UV detection 220 nm. The $t_R$ was 17.29 min and homogeneity by HPLC was >80%.

Mass Spectral Analysis

Performed on a MALDI-TOF "Vision 2000" mass spectrometer. Calculated MW is 2697.01 and MS MW was 2697.

(b) Synthesis of (R-2-FR-3-NP-1)$_2$-Lys-OH

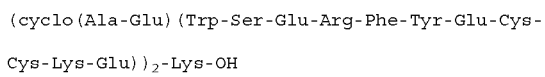
(cyclo(Ala-Glu)(Trp-Ser-Glu-Arg-Phe-Tyr-Glu-Cys-Cys-Lys-Glu))$_2$-Lys-OH For the synthesis of (R-2-FR-3-NP-1)$_2$-Lys-OH some of the peptidyl-polymer obtained in the previous synthesis of peptide (FR-3-NP-1)$_2$-Lys-OH (described in (a) above) in accordance with the protocol of the synthesizer's software package SyroXP Peptide was used.

Condensation with Cyclo(Ala-Glu(Trp-OH))

Dissolved 1.0 mmol of peptide (Ala-Glu(Trp-OH)) and 1.2 mmol of TBTU in DMF. To this solution added 1.2 mmol of N-ethyldiisopropylamine (DIPEA) and stirred at 0 degrees C. for 10 min. The reaction mixture was then transferred to a reactor containing the peptidyl-polymer from the synthesis of (FR-3-NP-1)$_2$-Lys-OH. The reaction was then carried out for 2 hours at room temperature with periodic stirring. The peptidyl-polymer was then filtered, and to it was added 10 ml of DMF and the peptidyl-polymer was mixed with the solvent in a reactor for 5 minutes. The peptidyl-polymer was then filtered, washed with 10 ml of ethanol and dried in air.

Preparation of Target Peptide (cyclo(Ala-Glu)(Trp-Ser-Glu-Arg-Phe-Tyr-Glu-Cys-Cys-Lys-Glu))$_2$-Lys-OH The dried peptidyl-polymer was transferred to a flask, to which then was added 3±0.1 ml of deblocking mixture: trifluoroacetic acid, thioanisole, phenol, water, ethanedithiol, triisopropylsilane in volumetric ratio 81.5/5/5/5/2.5/1 and stirred for 2 hours. The polymer was then filtered, and the solution was evaporated using a rotary evaporator. To the residue was added 20±1 ml of dry diethyl ether, transferred to a glass filter and filtered. The crude peptide precipitate was washed 20±1 ml of diethyl ether and dried in air.

Chromatographic Purification of (R-2-FR-3-NP-1)$_2$-Lys-OH

Purification was performed by reversed-phase high performance liquid chromatography (HPLC) using Phenomenex column 250×4.6 mm, sorbent Jupiter 5 μ C18 300 Å, eluent flow rate 1 ml/min. Gradient of acetonitrile in 0.1% TFA from 10% to 70% in 60 minutes. Speed 1 ml/min, t=20° C. UV detection 220 nm. The $t_R$ was 27.06 min and homogeneity by HPLC was >80%.

Mass Spectral Analysis

Performed on a MALDI-TOF "Vision 2000" mass spectrometer. Calculated MW is 3433.78 and MS MW was 3432.

III. Dosages and Methods of Administration of Peptides

Mice of the NMRI strain were immunized with the compounds (R-2-FR-3-NP-1)$_2$-Lys-OH and (FR-3-NP-1)2-Lys-OH according to the scheme shown in (Table 14).

The structures of the test compounds are shown in Table 15. The purity of the test substance was at least 97%.

Immunization was carried out in four stages. The peptide was dissolved in physiological saline and mixed with an equal volume of incomplete Freund's adjuvant (IFA) to obtain an emulsion. The emulsion was injected subcutaneously at the tail base in the amount of 0.2 ml per 100 μg (for the first immunization) and 50 μg of peptide (for the second, third and fourth immunization) per mouse. Prepared drugs for immunization were used with 25% excess due to inevitable losses when working with small amounts of emulsions.

IV. Simulation Method of Sporadic Form of Alzheimer's Disease Based on Bulbectomy A neurodegenerative process of the Alzheimer's type was initiated by removal of the olfactory bulbs of mice (bulbectomy). The operation was performed in sterile conditions under nembutal anaesthesia (40 mg/kg intraperitoneally). Subcutaneous administration of 0.5% solution of novocaine was performed as local anaesthesia for scalping. Bilateral removal of the olfactory bulbs was performed by aspiration through a burr hole in the skull with the coordinates: AP −3.5; L 0 (Copra, 1999). Sham-operated animals served as controls, which were subjected to the same procedure, but without the removal of the olfactory bulbs. All of the animals at the end of the operation were injected with the antibiotic Bicillin 5 in a dose of 6000 units in the hind leg muscles for the prevention of infection.

At the end of the behavioural experiments, anatomical control of the animals' brains was performed to check for completeness of the olfactory bulb removal.

V. Method for Studying Spatial Memory in Mice

The state of spatial memory was tested using the Morris maze water test as described in Example 1, Section IV (Materials and Methods).

For this study, mice were chosen as a species common for pre-clinical studies, NMRI strain with unknown haplotype, in which an animal model of Alzheimer's disease was developed. The number of animals used in these preliminary studies is sufficient for a preliminary assessment of the tested peptides, which is 36 mice, 5-7 mice in each group. The mice used in the study were NMRI mice obtained from the Vivarium institute of Cell Biophysics of the Russian Academy of Sciences. At the beginning of the administrations the mice were 2 months old and they weighed about 25 grams.

For immunization with preparations (FR-3-NP-1)$_2$-Lys-OH and (R-2-FR-3-NP-1)$_2$-Lys-OH, aliquots of the test substance were prepared. Saline solution and IFA were added to the aliquots in a 1:1 volume ratio and stirred to obtain a stable emulsion.

Mice were kept by groups in polycarbonate cages covered with latticed steel covers and feeders. The cages were changed periodically 1-2 times a week, and the animals were moved into disinfected cages with bedding, feeders and drinkers. Dirty cages, together with bedding, feeders and drinkers, were transferred to the disinfection and washing department of the vivarium for their further treatment.

Standard pelleted feed "Food for feeding laboratory rodents PC-120" (Russia, GOST) was placed into the feeders in latticed steel covers. Food brought into the barrier zone of animal housing was autoclaved.

Standard pelleted feed "Food for feeding laboratory rodents PC-120" (Russia, GOST) is placed into the feeders in latticed steel covers. Food brought into the barrier zone of animal housing is autoclaved.

Specially prepared filtered tap water was given ad libitum in standard autoclaved drinking bottles with steel lids-spouts. Water treatment ensured the absence of contamination, which could affect the results of the study.

The animals were kept in controlled ambient conditions (18-26° C. and 30-70% relative humidity). Temperature and humidity were continuously monitored in each experimental room and manually recorded once a day. In the animal rooms, 12-hour light cycle and at least a 10-time change of room air per hour were maintained.

Animals adapted/acclimatized in the vivarium for at least 5 days prior to the start of the administration. During this period, daily inspections of the animals' appearance were conducted. Animals with defects detected during the inspection were not included in the experimental group.

Animals without defects in appearance were selected for the experimental group, so that the individual weight value deviation from the mean value in the group did not exceed ±10%.

In one cage, was kept one group of animals of the same strain immunized with the same preparation according to the same scheme.

For the immunizations, four portions of each preparation were prepared: 1.5 mg in a test tube for the first immunization and 0.75 mg in test tubes for the $2^{nd}$, $3^{rd}$, and $4^{th}$ immunizations.

February 25: First Immunization

Group I: into the test tube with 1.5 mg of (FR-3-NP-1)$_2$-Lys-OH 1.5 ml of saline solution were added followed by 1.5 ml of IFA. The mixture was emulsified. 2.4 ml of prepared emulsion were taken into a syringe. Emulsion was injected into the mouse tail base at the rate of 200 μl per 1 mouse.

Group II: into the test tube with 1.5 mg of (R-2-FR-3-NP-1)$_2$-Lys-OH 1.5 ml of saline solution were added followed by 1.5 ml of IFA. The mixture was emulsified. 2.4 ml of prepared emulsion were taken into a syringe. Emulsion was injected into the mouse tail base at the rate of 200 μl per 1 mouse.

II, III, and IV Immunization

Group I: into the test tube with 0.75 mg of (FR-3-NP-1)$_2$-Lys-OH 1.5 ml of saline solution were added followed by 1.5 ml of IFA. The mixture was emulsified. 2.4 ml of prepared emulsion were taken into a syringe. Emulsion was injected into the mouse tail base at the rate of 200 μl per 1 mouse.

Group II: into the test tube with 0.75 mg of (R-2-FR-3-NP-1)$_2$-Lys-OH 1.5 ml of saline solution were added followed by 1.5 ml of IFA. The mixture was emulsified. 2.4 ml of prepared emulsion were taken into a syringe. Emulsion was injected into the mouse tail base at the rate of 200 μl per 1 mouse.

On the $22^{nd}$ day, corresponding to the interval between the second and third immunization, the mice's olfactory bulbs were removed. Non-immunized sham-operated (SO) and bulbectomized (BE) animals served as controls. Each group consisted of 5-8 mice. Earlier, it was discovered that after bulbectomy, the animals develop behavioural and biochemical signs of neurodegenerative process of Alzheimer's type: loss of spatial memory, increased level of cerebral beta-amyloid, acetylcholine and serotonergic brain system deficiency, low immune reactivity, loss of neurons in the brain areas responsible for learning and memory.

VI. Results

A month after bulbectomy, the mice were tested for state of spatial memory. Earlier, we discovered that BE mice of the NMRI strain in the month after the operation develop signs of neurodegeneration similar to AD, which is particularly manifested in the deterioration of spatial memory tested in the Morris water maze. It was of interest to investigate the effect of immunization with peptides (FR-3-NP-1)$_2$-Lys-OH and (R-2-FR-3-NP-1)$_2$-Lys-OH using incomplete Freund's adjuvant on the characteristics of spatial memory (time of residence in compartments of the Morris water maze and the number of visits into them) in bulboectomized animals in comparison with the effect of such immunization on the memory of control sham-operated mice.

Figure 4:
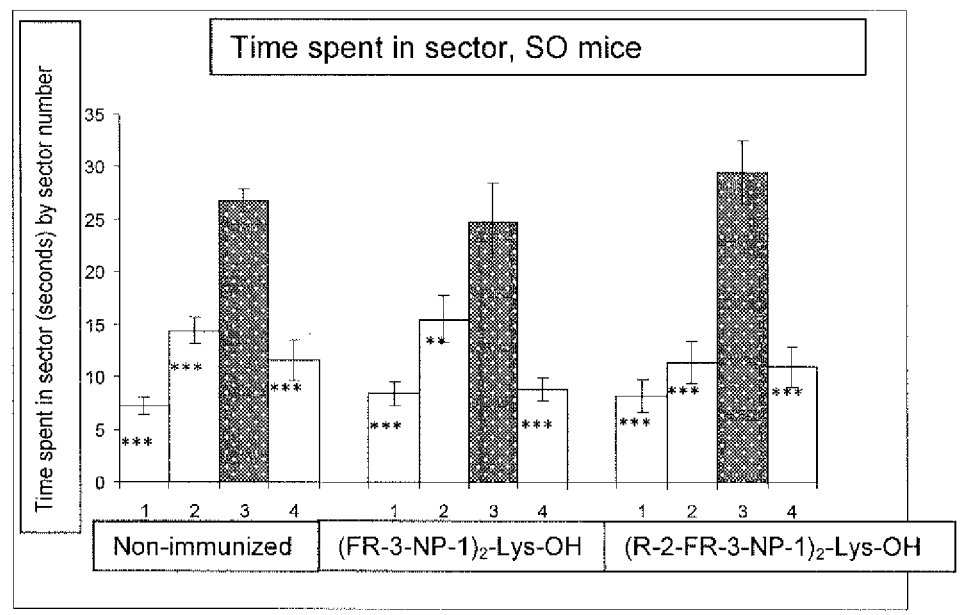
FIG. 4 shows the effect of immunization with peptides (FR-3-NP-1)$_2$-Lys-OH and (R-2-FR-3-NP-1)$_2$-Lys-OH on the spatial memory of sham-operated mice. A—data on time spent in compartments of Morris water maze. B—data on number of visits expressed in % of total number of visits during memory test to all sections of maze, calculated individually for each animal.
Figure 4:
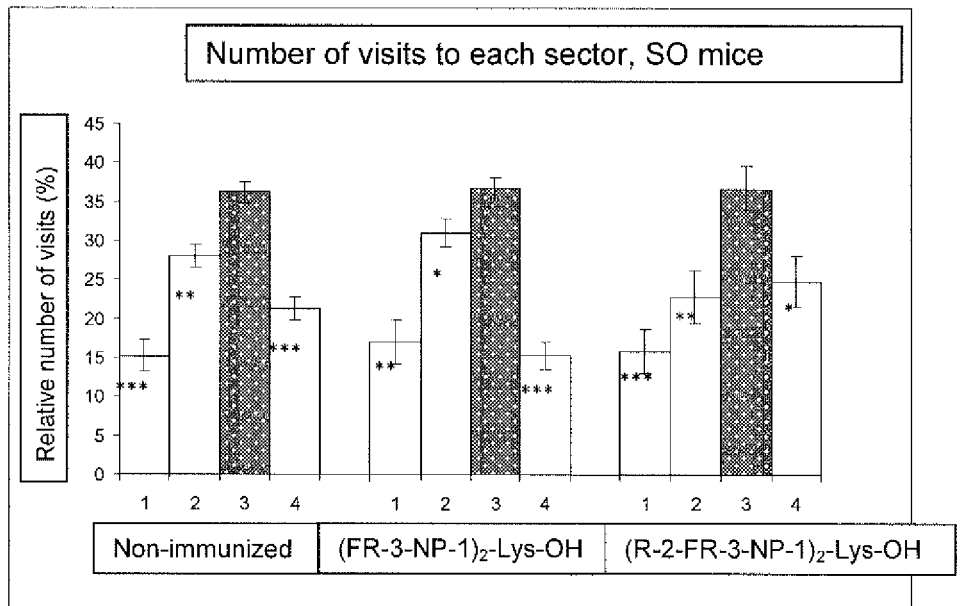

Immunization of SO mice with peptides (FR-3-NP-1)$_2$-Lys-OH and (R-2-FR-3-NP-1)$_2$-Lys-OH did not have a negative impact on their spatial memory, tested in the Morris water maze (FIGS. 4 A and B). The immunized SO animals, similar to control SO animals, with high confidence identified the compartment where the rescue platform was located during the training among three other indifferent compartments both in terms of residence time (FIG. 4A), and number of visits (FIG. 4B). It should be noted that both values were somewhat higher in the group of animals immunized with (R-2-FR-3-NP-1)$_2$-Lys-OH.

Figure 5:
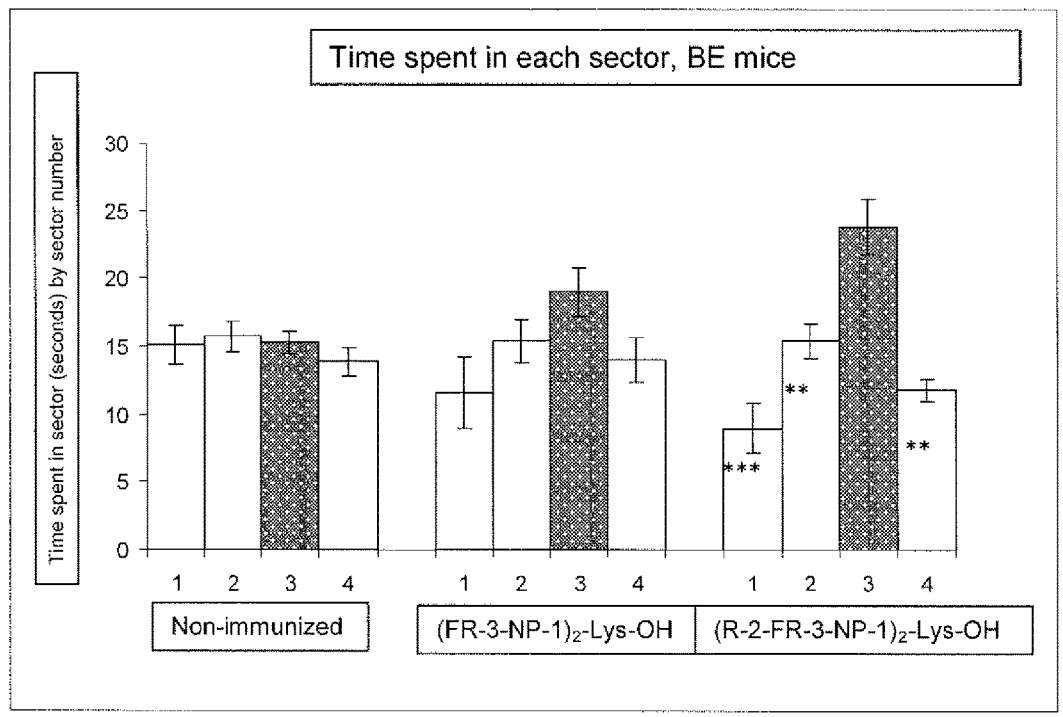
FIG. 5 shows the effect of immunization with peptides (FR-3-NP-1)$_2$-Lys-OH and (R-2-FR-3-NP-1)$_2$-Lys-OH on the spatial memory of bulbectomized mice. A—data on time spent in compartments of Morris water maze. B—data on number of visits expressed in % of total number of visits during memory test to all sections of maze, calculated individually for each animal.
Figure 5:
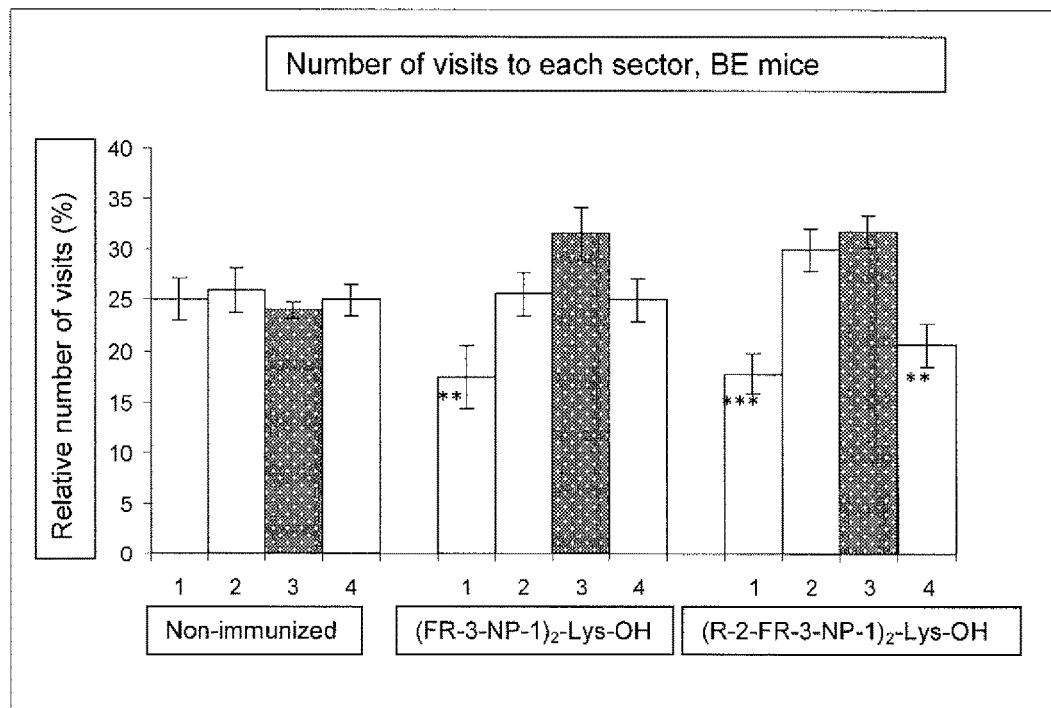

The BE mice immunized with the peptide (R-2-FR-3-NP-1)$_2$-Lys-OH showed improvement in spatial memory (FIG. 5). The most significant positive effect was recorded in terms of time spent in the training/rescue compartment—the animals selected the third compartment with statistical significance. The second, albeit smaller, positive effect was observed in terms of the number of visits to a given compartment—it was observed that the animals preferred the second and third compartments. In the BE mice group immunized with the peptide (FR-3-NP-1)$_2$-Lys-OH, both parameters (time spent in, and the number of visits to the training/rescue compartment) were much worse, and only a slight tendency towards improvement of spatial memory in comparison with a group of non-immunized BE mice was observed.

The study of the effect of immunization with peptides (FR-3-NP-1)$_2$-Lys-OH and (R-2-FR-3-NP-1)$_2$-Lys-OH using incomplete Freund's adjuvant on the characteristics of spatial memory in bulbectomized animals compared with the effect of such immunization on the memory of control sham-operated mice was conducted. It was demonstrated that the BE mice immunized with the peptide (R-2-FR-3-NP-1)$_2$-Lys-OH showed confirmed improvement of spatial memory. In the BE mice group immunized with the peptide (FR-3-NP-1)$_2$-Lys-OH, the values were much worse, and only a slight tendency of improvement of spatial memory in comparison with a group of non-immunized BE mice was observed.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

[1] Netzer, W. J et al., Lowering β-Amyloid Levels Rescues Learning and Memory in a Down Syndrome Mouse Model, PLoS ONE (2010) vol. 5(6), e10943.

[2] Zhang, Y. et al., Mutant Ubiquitin-Mediated β-secretase Stability via Activation of Caspase-3 is Related to β-amyloid Accumulation in Ischemic Striatum in Rats, Journal of Cerebral Blood Flow & Metabolism (2010) vol. 30, pp. 566-575.

[3] Giunta, B. et al., Antiretroviral Medications Disrupt Microglial Phagocytosis of β-amyloid and Increase its Production by Neurons: Implications for HIV-associated Neurocognitive Disorders, Molecular Brain (2011) vol. 4, 23.

[4] Loane, D. J. et al., Modulation of ABCA1 by an LXR Agonist Reduces Beta-Amyloid Levels and Improves Outcome after Traumatic Brain injury, Journal of Neurotrauma (2011) vol. 28, pp. 225-236.

[5] Roberts, G. W. et al., βA4 amyloid protein deposition in brain after head trauma, Lancet (1991) vol. 338, pp. 1422-1423.

[6] Ikonomovic, M. D. et al., Alzheimer's pathology in human temporal cortex surgically excised after severe brain injury, Exp. Neurol. (2004) vol. 190, pp. 192-203.

[7] Zhang, Y. et al., Reduction of β-amyloid deposits by γ-secretase inhibitor is associated with the attenuation of secondary damage in the ipsilateral thalamus and sensory functional improvement after focal cortical infarction in hypertensive rats, Journal of Cerebral Blood Flow & Metabolism (2011), vol. 31, pp. 572-579.

[8] McKee, A. G. et al., Chronic Traumatic Encephalopathy in Athletes: Progressive Tauopathy following Repetitive Head Injury, J. Neuropathol. Exp. Neurol. (2009) vol. 68(7), pp. 709-735.

[9] Watkins, P. B. et al., J. Am. Med. Assoc. (1994) vol. 271, pp. 992-998.

[10] Raina, P. et al., Ann. Intern. Med. (2008) vol. 148(5), pp. 379-397.

[11] Nagele, R. G., D'Andrea, M. R., Anderson, W. J., Wang, H. Y., Neuroscience (2002) vol. 110, pp. 199-211.

TABLE 1

| Analytical data for R-1-NP-1 | |
|---|---|
| Molecular formula | $C_{131}H_{190}N_{34}O_{38}S_2$ |
| Chemical structure | cyclo(Ala-Glu)-Trp-(Glu-Trp-Asp-Leu-Val-Gly-Ile-Pro-Gly-Lys-Arg-Ser-Glu-Arg-Phe-Tyr-Cys-Cys-Lys-Glu) |
| Molecular mass, Da | 2913.3 |

TABLE 2

| Analytical results for R-1-NP-1 | | | | |
|---|---|---|---|---|
| Analysis | Method | Requirements | Results | Confirmation |
| HPLC purity | Phenomenex Jupiter 5μ, C18 300A (250 × 4.6 mm) 5 microns Eluent A: 0.1% TFA Eluent B: 0.1% TFA/acetonitrile Gradient: 10→70% B in 60 min. Flow rate 1 ml/min, t = 20° C. Detection UV 226 nm | >95% | 98%, $t_R$ = 27.12 min | corresponds |
| Molecular ion (m/z) | MALDI-TOF "Vision 2000" | 2913 ± 1 | 2913 | corresponds |

TABLE 3

| Day | Group I (12 mice) NP-1 with IFA | Group II (12 mice) R-1-NP-1 with IFA |
|---|---|---|
| 1 | 1st immunization, 0.1 mg/animal | 1st immunization, 0.1 mg/animal |
| 12 | 2nd immunization, 0.05 mg/animal | 2nd immunization, 0.05 mg/animal |
| 18 | bulbectomy operation (7 operated (BE) and 5 sham-operated (SO) mice) | |
| 23 | 3rd immunization, 0.05 mg/animal | 3rd immunization, 0.05 mg/animal |
| 37 | 4th immunization, 0.05 mg/animal | 4th immunization, 0.05 mg/animal |
| 47 | start of education | |
| 53 | memory testing, collection of blood serum, cerebrospinal fluid and brain structures | |

TABLE 4

| Mouse Group | F | Time spent in sector (seconds) | | | |
|---|---|---|---|---|---|
| | | 1 | 2 | 3[1] | 4 |
| FO | F = 16.58*** | 7.8 ± 2.13*** | 12 ± 1.41** | 30.2 ± 3.57 | 10 ± 2.49** |
| | P = 3.64E−05 | | | | |
| FO + NP-1 | F = 22.8*** | 10.5 ± 2.25*** | 13 ± 1.68*** | 27.5 ± 1.5 | 9 ± 1.58*** |
| | P = 3.03E−05 | | | | |
| FO + R-1-NP1 | F = 24.09*** | 7.2 ± 1.83*** | 14 ± 2.43*** | 30.41 ± 2.42 | 8.4 ± 1.96*** |
| | P = 3.56E−06 | | | | |
| BE | F = 2.89 | 12 ± 1.2 | 18.71 ± 1.8 | 15.71 ± 1.6 | 13.57 ± 2.11 |
| | P = 0.056112 | | | | |
| BE + NP-1 | F = 2.4 | 17 ± 0.84 | 15.2 ± 1.69 | 16 ± 11.14 | 11.8 ± 1.91 |
| | P = 0.105651 | | | | |
| BE + R-1-NP-1 | F = 7.9** | 12.17 ± 2.06* | 13.67 ± 1.5* | 25.33 ± 4.02 | 8.83 ± 1.85** |
| | P = 0.001136 | | | | |

[1] Training sector with platform.
Table 4 shows the statistical significance of the selection of sector 3 (training sector) as compared to other sectors (1, 2 and 4):
*$p < 0.05$;
**$p < 0.01$;
***$p < 0.001$.

TABLE 5

| Mouse Group | F | Ratio of sector visits to total number of all visits (as percentage) | | | |
|---|---|---|---|---|---|
| | | 1 | 2 | 3[1] | 4 |
| FO | F = 32.09*** | 12.8 ± 2.11*** | 26 ± 1.41** | 37.4 ± 2.38 | 24.2 ± 0.73** |
| | P = 5.31E−07 | | | | |
| FO + NP-1 | F = 24.8*** | 14.5 ± 1.89*** | 27.5 ± 2.1* | 40.75 ± 3.15 | 18 ± 2.08** |
| | P = 1.98E−05 | | | | |
| FO + R-1-NP1 | F = 17.22*** | 12.4 ± 2.7*** | 26 ± 2.86** | 40 ± 2.19 | 22.2 ± 3.18** |
| | P = 2.91E−05 | | | | |
| BE | F = 4.33* | 22.29 ± 2.52 | 30.71 ± 1.73 | 25.43 ± 1.74 | 21.57 ± 1.9 |
| | P = 0.014206 | | | | |
| BE + NP-1 | F = 3.62* | 26.6 ± 1.54 | 27.8 ± 2.06 | 24.2 ± 0.49 | 21.2 ± 1.6 |
| | P = 0.036222 | | | | |
| BE + R-1-NP-1 | F = 13.75*** | 20.67 ± 2.2** | 27 ± 1.46* | 34.33 ± 2.44 | 18.17 ± 1.49*** |
| | P = 4.27E−05 | | | | |

[1] Training sector with platform.
Table 5 shows the statistical significance of the selection of sector 3 (training sector) by relative visits as compared to other sectors (1, 2 and 4):
*$p < 0.05$;
**$p < 0.01$;
***$p < 0.001$.

TABLE 6

| | Individual Sera | | | | | Pool |
|---|---|---|---|---|---|---|
| titer (-lg) | 2.2 | <1.3 | 3.1 | 3.4 | 3.4 | 2.8 |
| dilution | 1:160 | <1:20 | 1:1280 | 1:2560 | 1:2560 | 1:640 |

TABLE 7

| | Individual Sera | | | | | Pool |
|---|---|---|---|---|---|---|
| titer (-lg) | 3.4 | 3.4 | 3.4 | 3.4 | 2.5 | 3.4 |
| dilution | 1:2560 | 1:2560 | 1:2560 | 1:2560 | 1:320 | 1:2560 |

TABLE 8

| | Individual Sera | | | | | Pool |
|---|---|---|---|---|---|---|
| titer (-lg) | 2.2 | 3.1 | 3.1 | 2.8 | 2.8 | 3.1 |
| dilution | 1:160 | 1:1280 | 1:1280 | 1:640 | 1:640 | 1:1280 |

TABLE 9

| | Individual Sera | | | | | | | Pool |
|---|---|---|---|---|---|---|---|---|
| titer (-lg) | 2.5 | 3.1 | 2.5 | 3.1 | <1.3 | 3.7 | 2.8 | 3.1 |
| dilution | 1:320 | 1:1280 | 1:320 | 1:1280 | <1:20 | 1:5120 | 1:640 | 1:1280 |

TABLE 10

| Group | Mouse No. | Individual levels of βA (ng/g tissue) | Average level of βA (ng/g tissue) |
|---|---|---|---|
| FO | 44 | 2.305 | 2.36 ± 0.04 |
| | 45 | 2.438 | FO-BE*** |
| | 46 | 2.229 | P = 7.154E−10 |
| | 47 | 2.378 | |
| | 48 | 2.478 | |
| BE | 37 | 8.71 | 8.35 ± 0.11 |
| | 38 | 8.024 | |
| | 39 | 8.576 | |
| | 41 | 8.294 | |

TABLE 10-continued

| Group | Mouse No. | Individual levels of βA (ng/g tissue) | Average level of βA (ng/g tissue) |
|---|---|---|---|
| | 42 | 8.385 | |
| | 43 | 8.114 | |
| FO + R-1-NP-1 | 20 | 3.362 | 2.78 ± 0.21 |
| | 21 | 3.058 | FO-FO$_{R\text{-}1\text{-}NP\text{-}1}$ |
| | 22 | 2.208 | not stat. sig. |
| | 23 | 2.418 | P = 0.12 |
| | 24 | 2.834 | |
| BE + R-1-NP-1 | 13 | 2.525 | 2.985 ± 0.2 |
| | 14 | 3.704 | BE-BE$_{R\text{-}1\text{-}NP\text{-}1}$*** |
| | 15 | 3.705 | P = 1.64E−09 |
| | 16 | 2.398 | |
| | 17 | 2.91 | |
| | 18 | 2.77 | |
| | 19 | 2.882 | |
| FO + NP-1 | 8 | 4.028 | 3.22 ± 0.38 |
| | 9 | 4.009 | FO-FO$_{NP\text{-}1}$ |
| | 10 | 2.549 | not stat. sig. |
| | 11 | 3.380 | P = 0.09 |
| | 12 | 2.118 | |
| BE + NP-1 | 1 | 3.039 | 2.44 ± 0.38 |
| | 2 | 2.316 | BE-BE$_{NP\text{-}1}$*** |
| | 3 | 3.324 | P = 4.26E−05 |
| | 5 | 1.115 | |
| | 6 | 2.408 | |

Significance:
***p < 0.001

TABLE 11

| Day # | |
|---|---|
| 1 | 1st immunization with CFA, 0.1 mg/mouse |
| 24 | Bulbectomy operation |
| 44 | 2nd immunization with IFA, 0.1 mg/mouse |
| 54 | Beginning of education |
| 58 | Memory testing, blood collection |

TABLE 12

| | | Time spent in sector (seconds) | | | |
|---|---|---|---|---|---|
| Mouse Group | F | 1 | 2 | 3 training sector (with platform) | 4 |
| FO | F = 36.75*** P = 7.62E−10 | 7.33 ± 1.31*** | 14.56 ± 1.0*** | 30.0 ± 2.31 | 8.0 ± 1.3*** |
| BE | F = 2.51 P = 0.08 | 13.89 ± 2.19 | 19.0 ± 2.38 | 15.44 ± 1.49 | 11.56 ± 1.7 |
| BE + FR-1-NP-1 (173-188) | F = 4.02* P = 0.021601 | 15.83 ± 2.88 | 17.0 ± 2.21 | 18.33 ± 2.04 | 8.83 ± 0.7** |
| BE + FR-2-NP-1 (179-188) | F = 8.09** P = 0.001007 | 12.33 ± 2.38* | 18.33 ± 1.82 | 20.1 ± 1.86 | 8.33 ± 1.98*** |
| BE + FR-3-NP-1 (184-193) | F = 9.41** P = 0.001784 | 13.0 ± 1.91* | 13.75 ± 2.1* | 25.25 ± 3.47 | 8.0 ± 1.58** |

Table 12 shows the statistical significance of the selection of sector 3 (training sector) as compared to other sectors (112 and 4):
*p < 0.05;
**p < 0.01;
***p < 0.001.

TABLE 13

| | | Ratio of sector visits to total number of all visits (as percentage) | | | |
|---|---|---|---|---|---|
| Mouse Group | F | 1 | 2 | 3 training sector (with platform) | 4 |
| FO | F = 36.22*** P = 8.95E−10 | 13.11 ± 2.24*** | 32.11 ± 1.56** | 40.44 ± 2.1 | 14.56 ± 2.04*** |
| BE | F = 2.34 P = 0.092325 | 21.78 ± 1.94 | 28.56 ± 1.62 | 27.22 ± 2.36 | 22.78 ± 2.61 |
| BE + FR-1-NP-1 (173-188) | F = 8.05** P = 0.001029 | 22.17 ± 2.63* | 30.17 ± 1.49 | 30.83 ± 2.32 | 18.33 ± 1.74** |
| BE + FR-2-NP-1 (179-188) | F = 22.71*** P = 1.19E−06 | 17.17 ± 2.32*** | 34.5 ± 2.05 | 35.51 ± 2.64 | 13.67 ± 2.53*** |

TABLE 13-continued

Ratio of sector visits to total number of all visits (as percentage)

| Mouse Group | F | 1 | 2 | 3 training sector (with platform) | 4 |
|---|---|---|---|---|---|
| BE + FR-3-NP-1 (184-193) | F = 3.27 P = 0.058824 | 20.75 ± 1.25 | 26.25 ± 2.95 | 32.0 ± 4.3 | 21.0 ± 2.38 |

Table 13 shows the statistical significance of the selection of sector 3 (training sector) by relative visits as compared to other sectors (1, 2 and 4):
*p < 0.05;
**p < 0.01;
***p < 0.001.

TABLE 14

| Day | Date | I group (FR-3-NP-1)$_2$-Lys-OH (into IFA) 7 BE + 5 SO | II group (R-2-FR-3-NP-1)$_2$-Lys-OH (into IFA) 7 BE + 5 FO |
|---|---|---|---|
| Day 1 | February 25 (Monday) | 1 immunization, 0.1 mg/animal | |
| Day 15 | March 11 (Monday) | II immunization, 0.05 mg/animal | |
| Day 22 | March 18 (Monday) | Bulbectomy | |
| Day 26 | March 22 (Friday) | III immunization, 0.05 mg/animal | |
| Day 38 | April 3 (Wednesday) | IV immunization, 0.05 mg/animal | |
| Day 50 | April 15 (Monday) | Beginning of training | |
| Day 54 | April 19 (Friday) | Memory test | |
| Day 57 | April 22 (Monday) | | |

TABLE 15

| Short name | Formula |
|---|---|
| (FR-3-NP-1)$_2$-Lys-OH | Ser-Glu-Arg-Phe-Tyr-Glu-Cys-Cys-Lys-Glu-Lys(Ser-Glu-Arg-Phe-Tyr-Glu-Cys-Cys-Lys-Glu)-OH |
| (R-2-FR-3-NP-1)$_2$-Lys-OH | (cyclo(Ala-Glu)(Trp-Ser-Glu-Arg-Phe-Tyr-Glu-Cys-Cys-Lys-Glu))$_2$-Lys-OH |

We claim:

1. A compound of Formula I:

[$R^a$-NP]$_m$-L$_p$ (I)

wherein
 NP is a sequence comprising at least 9 contiguous amino acids of Glu-Trp-Asp-Leu-Val-Gly-Ile-Pro-Gly-Lys-Arg-Ser-Glu-Arg-Phe-Tyr-Glu-Cys-Cys-Lys-Glu [SEQ ID NO:1], optionally with conservative amino acid substitutions or amino acid analog substitutions thereof, or
 NP is a deletion or addition analog of [SEQ ID NO:1], optionally with conservative amino acid substitutions or amino acid analog substitutions thereof;
 m is 1 or 2;
 p is 0 when m is 1 and p is 1 when m is 2;
 L is a linker group that connects the two $R^a$-NP groups when m is 2;
 $R^a$ is a group of the formula:

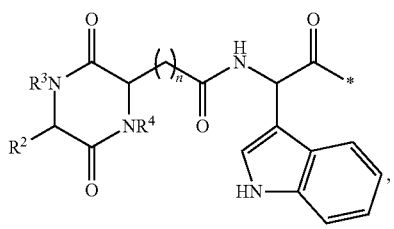

wherein
 * represents the site of attachment to NP;
 n is 1 or 2;
 $R^2$ is $C_{1-6}$alkyl or $C_{1-3}$alkylenePh; and
 $R^3$ and $R^4$ are independently selected from H and $C_{1-4}$alkyl,
or pharmaceutically acceptable salts thereof.

2. The compound of claim 1, wherein NP is selected from:

| | |
|---|---|
| EWDLVGIPGKRSERFYECCKE; | [SEQ ID NO: 1] |
| WDLVGIPGKRSERFYECCKE; | [SEQ ID NO: 2] |
| DLVGIPGKRSERFYECCKE; | [SEQ ID NO: 3] |
| LVGIPGKRSERFYECCKE; | [SEQ ID NO: 4] |
| VGIPGKRSERFYECCKE; | [SEQ ID NO: 5] |
| GIPGKRSERFYECCKE; | [SEQ ID NO: 6] |
| IPGKRSERFYECCKE; | [SEQ ID NO: 7] |
| PGKRSERFYECCKE; | [SEQ ID NO: 8] |
| GKRSERFYECCKE; | [SEQ ID NO: 9] |

-continued

KRSERFYECCKE; [SEQ ID NO: 10]

RSERFYECCKE; [SEQ ID NO: 11]

SERFYECCKE; [SEQ ID NO: 12]

ERFYECCKE; [SEQ ID NO: 13]

EWDLVGIPGKRSERFYECCK; [SEQ ID NO: 14]

EWDLVGIPGKRSERFYECC; [SEQ ID NO: 15]

EWDLVGIPGKRSERFYEC; [SEQ ID NO: 16]

EWDLVGIPGKRSERFYE; [SEQ ID NO: 17]

EWDLVGIPGKRSERFY; [SEQ ID NO: 18]

EWDLVGIPGKRSERF; [SEQ ID NO: 19]

EWDLVGIPGKRSER; [SEQ ID NO: 20]

EWDLVGIPGKRSE; [SEQ ID NO: 21]

EWDLVGIPGKRS; [SEQ ID NO: 22]

EWDLVGIPGKR; [SEQ ID NO: 23]

EWDLVGIPGK; [SEQ ID NO: 24]

EWDLVGIPG; [SEQ ID NO: 25]

WDLVGIPGK; [SEQ ID NO: 26]

EWDLVGIPGKRSERFY; and [SEQ ID NO: 27]

IPGKRSERFY, [SEQ ID NO: 28]

and
conservative amino acid substitutions thereof.

3. The compound of claim 2, wherein NP is NP-1 [SEQ ID NO:1] or FR-3-NP-1 [SEQ ID NO:12].

4. The compound of claim 1, wherein m is 1.

5. The compound of claim 1, wherein L is lysine, serine, threonine, aspartic acid or glutamic acid.

6. The compound of claim 1, wherein m is 2 and L is a di-amino or di-hydroxy $C_{1-20}$alkylene.

7. The compound of claim 1, wherein $R^a$ is a group of the formula:

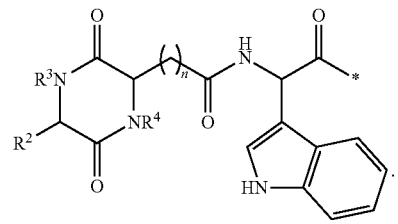

8. The compound of claim 7, wherein n is 1 or 2.

9. The compound of claim 7, wherein $R^2$ is $C_{1-6}$alkyl or $CH_2Ph$.

10. The compound of claim 7, wherein $R^3$ and $R^4$ are independently selected from H and $CH_3$.

11. The compound of claim 1, wherein the stereochemistry of all amino acids in the compound of Formula I is the natural, or L, configuration.

12. The compound of claim 1, selected from R-1-NP-1, [R-2-NP-1]$_2$-Lys-OH, [R-2-FR-1-NP-1]$_2$-Lys-OH, [R-2-FR-2-NP-1]$_2$-Lys-OH and [R-2-FR-3-NP-1]$_2$-Lys-OH.

13. The compound of claim 1, wherein m is 1 and p is 0, and the compound of Formula I is:

$$R^a\text{-NP} \qquad\qquad\qquad I,$$

wherein
NP is a sequence comprising at least 9 contiguous amino acids of Glu-Trp-Asp-Leu-Val-Gly-Ile-Pro-Gly-Lys-Arg-Ser-Glu-Arg-Phe-Tyr-Glu-Cys-Cys-Lys-Glu [SEQ ID NO:1], optionally with conservative amino acid substitutions or amino acid analog substitutions thereof, or
NP is a deletion or addition analog of [SEQ ID NO:1], optionally with conservative amino acid substitutions or amino acid analog substitutions thereof; and
$R^a$ is a group of the formula:

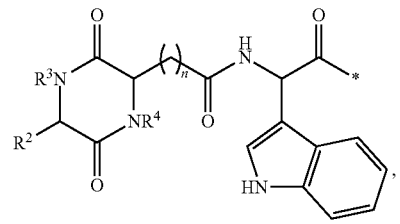

wherein
* represents the site of attachment to NP;
n is 1 or 2;
$R^2$ is $C_{1-6}$alkyl or $C_{1-3}$alkylenePh; and
$R^3$ and $R^4$ are independently selected from H and $C_{1-4}$alkyl,
or pharmaceutically acceptable salts thereof.

14. The compound of claim 1, conjugated to a protein carrier.

15. A pharmaceutical composition comprising one or more compounds of claim 1 and a pharmaceutically acceptable carrier.

16. The pharmaceutical composition of claim 15, further comprising an adjuvant.

17. A method of treating diseases, disorders or conditions characterized by or associated with β-amyloid accumulation comprising administering a therapeutically effective amount of one or more compounds of claim 1 to a subject in need thereof.

18. The method of claim 17, wherein the disease, disorder or condition characterized by or associated with β-amyloid accumulation is selected from Alzheimer's disease, Down syndrome, transient cerebral ischemia, HIV infection, traumatic brain injury, cerebral cortical infarction and chronic traumatic encephalopathy.

19. The method of claim 18, wherein the disease, disorder or condition characterized by or associated with β-amyloid accumulation is Alzheimer's disease.

20. The compound of claim 1, wherein m is 2 and L is an amino acid in which one $R^a$-NP group is attached at the amino position and another $R^a$-NP group is attached to a functional group in the side chain.

* * * * *

SEQUENCE LISTING

```
<160> NUMBER OF SEQ ID NOS: 28

<210> SEQ ID NO 1
<211> LENGTH: 21
<212> TYPE: PRT
<213> ORGANISM: Artificial Sequence
<220> FEATURE:
<223> OTHER INFORMATION: Synthetic

<400> SEQUENCE: 1

Glu Trp Asp Leu Val Gly Ile Pro Gly Lys Arg Ser Glu Arg Phe Tyr
1               5                   10                  15

Glu Cys Cys Lys Glu
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic

<400> SEQUENCE: 2

Trp Asp Leu Val Gly Ile Pro Gly Lys Arg Ser Glu Arg Phe Tyr Glu
1               5                   10                  15

Cys Cys Lys Glu
```

-continued

```
<210> SEQ ID NO 3
<211> LENGTH: 19
<212> TYPE: PRT
<213> ORGANISM: Artificial Sequence
<220> FEATURE:
<223> OTHER INFORMATION: Synthetic

<400> SEQUENCE: 3

Asp Leu Val Gly Ile Pro Gly Lys Arg Ser Glu Arg Phe Tyr Glu Cys
1               5                   10                  15

Cys Lys Glu

<210> SEQ ID NO 4
<211> LENGTH: 18
<212> TYPE: PRT
<213> ORGANISM: Artificial Sequence
<220> FEATURE:
<223> OTHER INFORMATION: Synthetic

<400> SEQUENCE: 4

Leu Val Gly Ile Pro Gly Lys Arg Ser Glu Arg Phe Tyr Glu Cys Cys
1               5                   10                  15

Lys Glu

<210> SEQ ID NO 5
<211> LENGTH: 17
<212> TYPE: PRT
<213> ORGANISM: Artificial Sequence
<220> FEATURE:
<223> OTHER INFORMATION: Synthetic

<400> SEQUENCE: 5

Val Gly Ile Pro Gly Lys Arg Ser Glu Arg Phe Tyr Glu Cys Cys Lys
1               5                   10                  15

Glu

<210> SEQ ID NO 6
<211> LENGTH: 16
<212> TYPE: PRT
<213> ORGANISM: Artificial Sequence
<220> FEATURE:
<223> OTHER INFORMATION: Synthetic

<400> SEQUENCE: 6

Gly Ile Pro Gly Lys Arg Ser Glu Arg Phe Tyr Glu Cys Cys Lys Glu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Ile Pro Gly Lys Arg Ser Glu Arg Phe Tyr Glu Cys Cys Lys Glu
1               5                   10                  15

<210> SEQ ID NO 8
<211> LENGTH: 14
<212> TYPE: PRT
<213> ORGANISM: Artificial Sequence
<220> FEATURE:
```

<223> OTHER INFORMATION: Synthetic

<400> SEQUENCE: 8

Pro Gly Lys Arg Ser Glu Arg Phe Tyr Glu Cys Cys Lys Glu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic

<400> SEQUENCE: 9

Gly Lys Arg Ser Glu Arg Phe Tyr Glu Cys Cys Lys Glu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Lys Arg Ser Glu Arg Phe Tyr Glu Cys Cys Lys Glu
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Arg Ser Glu Arg Phe Tyr Glu Cys Cys Lys Glu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Ser Glu Arg Phe Tyr Glu Cys Cys Lys Glu
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Glu Arg Phe Tyr Glu Cys Cys Lys Glu
1               5

<210> SEQ ID NO 14
<211> LENGTH: 20
<212> TYPE: PRT
<213> ORGANISM: Artificial Sequence
<220> FEATURE:
<223> OTHER INFORMATION: Synthetic

```
<400> SEQUENCE: 14

Glu Trp Asp Leu Val Gly Ile Pro Gly Lys Arg Ser Glu Arg Phe Tyr
1               5                   10                  15

Glu Cys Cys Lys
            20

<210> SEQ ID NO 15
<211> LENGTH: 19
<212> TYPE: PRT
<213> ORGANISM: Artificial Sequence
<220> FEATURE:
<223> OTHER INFORMATION: Synthetic

<400> SEQUENCE: 15

Glu Trp Asp Leu Val Gly Ile Pro Gly Lys Arg Ser Glu Arg Phe Tyr
1               5                   10                  15

Glu Cys Cys

<210> SEQ ID NO 16
<211> LENGTH: 18
<212> TYPE: PRT
<213> ORGANISM: Artificial Sequence
<220> FEATURE:
<223> OTHER INFORMATION: Synthetic

<400> SEQUENCE: 16

Glu Trp Asp Leu Val Gly Ile Pro Gly Lys Arg Ser Glu Arg Phe Tyr
1               5                   10                  15

Glu Cys

<210> SEQ ID NO 17
<211> LENGTH: 17
<212> TYPE: PRT
<213> ORGANISM: Artificial Sequence
<220> FEATURE:
<223> OTHER INFORMATION: Synthetic

<400> SEQUENCE: 17

Glu Trp Asp Leu Val Gly Ile Pro Gly Lys Arg Ser Glu Arg Phe Tyr
1               5                   10                  15

Glu

<210> SEQ ID NO 18
<211> LENGTH: 16
<212> TYPE: PRT
<213> ORGANISM: Artificial Sequence
<220> FEATURE:
<223> OTHER INFORMATION: Synthetic

<400> SEQUENCE: 18

Glu Trp Asp Leu Val Gly Ile Pro Gly Lys Arg Ser Glu Arg Phe Tyr
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Glu Trp Asp Leu Val Gly Ile Pro Gly Lys Arg Ser Glu Arg Phe
1               5                   10                  15
```

<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

Glu Trp Asp Leu Val Gly Ile Pro Gly Lys Arg Ser Glu Arg
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic

<400> SEQUENCE: 21

Glu Trp Asp Leu Val Gly Ile Pro Gly Lys Arg Ser Glu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Glu Trp Asp Leu Val Gly Ile Pro Gly Lys Arg Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic

<400> SEQUENCE: 23

Glu Trp Asp Leu Val Gly Ile Pro Gly Lys Arg
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Glu Trp Asp Leu Val Gly Ile Pro Gly Lys
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Glu Trp Asp Leu Val Gly Ile Pro Gly
1               5

```
<210> SEQ ID NO 26
<211> LENGTH: 9
<212> TYPE: PRT
<213> ORGANISM: Artificial Sequence
<220> FEATURE:
<223> OTHER INFORMATION: Synthetic

<400> SEQUENCE: 26

Trp Asp Leu Val Gly Ile Pro Gly Lys
1               5

<210> SEQ ID NO 27
<211> LENGTH: 16
<212> TYPE: PRT
<213> ORGANISM: Artificial Sequence
<220> FEATURE:
<223> OTHER INFORMATION: Synthetic

<400> SEQUENCE: 27

Glu Trp Asp Leu Val Gly Ile Pro Gly Lys Arg Ser Glu Arg Phe Tyr
1               5                   10                  15

<210> SEQ ID NO 28
<211> LENGTH: 10
<212> TYPE: PRT
<213> ORGANISM: Artificial Sequence
<220> FEATURE:
<223> OTHER INFORMATION: Synthetic

<400> SEQUENCE: 28

Ile Pro Gly Lys Arg Ser Glu Arg Phe Tyr
1               5                   10
```